(12) United States Patent
Defieber et al.

(10) Patent No.: US 9,198,422 B2
(45) Date of Patent: Dec. 1, 2015

(54) PESTICIDAL PYRAZOLE COMPOUNDS

(75) Inventors: Christian Defieber, Mannheim (DE);
Sebastian Soergel, Ludwigshafen (DE);
Daniel Saelinger, Ludwigshafen (DE);
Ronan Le Vezouet, Mannheim (DE);
Karsten Koerber, Eppelheim (DE);
Steffen Gross, Ludwigshafen (DE);
Deborah L. Culbertson, Fuquay Varina, NC (US); Koshi Gunjima, Cary, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/112,619

(22) PCT Filed: Apr. 16, 2012

(86) PCT No.: PCT/EP2012/056875
§ 371 (c)(1),
(2), (4) Date: Oct. 18, 2013

(87) PCT Pub. No.: WO2012/143317
PCT Pub. Date: Oct. 26, 2012

(65) Prior Publication Data
US 2014/0045690 A1    Feb. 13, 2014

Related U.S. Application Data

(60) Provisional application No. 61/477,620, filed on Apr. 21, 2011.

(51) Int. Cl.
| | | |
|---|---|---|
| *A61K 31/50* | (2006.01) | |
| *A61K 31/501* | (2006.01) | |
| *A01N 43/58* | (2006.01) | |
| *C07D 401/14* | (2006.01) | |
| *C07D 403/12* | (2006.01) | |
| *C07D 405/14* | (2006.01) | |
| *C07D 409/14* | (2006.01) | |
| *C07D 411/14* | (2006.01) | |
| *C07D 417/14* | (2006.01) | |
| *A01N 43/56* | (2006.01) | |

(52) U.S. Cl.
CPC .............. *A01N 43/58* (2013.01); *A01N 43/56* (2013.01); *C07D 401/14* (2013.01); *C07D 403/12* (2013.01); *C07D 405/14* (2013.01); *C07D 409/14* (2013.01); *C07D 411/14* (2013.01); *C07D 417/14* (2013.01)

(58) Field of Classification Search
None
See application file for complete search history.

(56) References Cited

U.S. PATENT DOCUMENTS 8,729,083 B2 * 5/2014 Groß et al. ............... 514/252.05
2010/0305124 A1   12/2010 Fusslein et al.

FOREIGN PATENT DOCUMENTS

| EP | WO 2010034737 | * 4/2010 | ........... C07D 403/12 |
|---|---|---|---|
| WO | WO 2009/027393 | 3/2009 | |
| WO | WO 2010/034737 | 4/2010 | |
| WO | WO 2010/034738 | 4/2010 | |
| WO | WO 2010/112177 | 10/2010 | |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Preliminary Report on Patentability dated Oct. 22, 2013, prepared in International Application No. PCT/EP2012/056875.
International Search Report dated Jun. 13, 2012, prepared in International Application No. PCT/EP2012/056875.

* cited by examiner

Primary Examiner — Jeffrey H Murray
(74) Attorney, Agent, or Firm — Brinks Gilson & Lione

(57) ABSTRACT

The present invention relates to novel pyrazoles of formula I wherein the variables are as defined in the description, a method for controlling invertebrate pests, a method for protecting plant propagation material and/or the plants which grow therefrom, to plant propagation material, comprising at least one compound according to the present invention, and to an agricultural composition.

20 Claims, No Drawings

PESTICIDAL PYRAZOLE COMPOUNDS

This application is a National Stage application of International Application No. PCT/EP2012/056875, filed Apr. 16, 2012, which claims the benefit of U.S. Provisional Application No. 61/477,620, filed Apr. 21, 2011, the entire contents of which are hereby incorporated herein by reference.

The present invention relates to novel pyrazoles of formula I

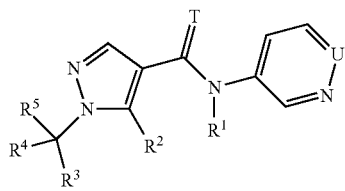

I wherein
U is N or CH;
T is O or S;
$R^1$ is H, $C_1$-$C_2$-alkyl, or $C_1$-$C_2$-alkoxy-$C_1$-$C_2$-alkyl;
$R^2$ is $CH_3$, or halomethyl;
$R^3$ is $C_2$-$C_6$-alkyl, $C_1$-$C_6$-haloalkyl, $C_1$-$C_2$-alkoxy-$C_1$-$C_2$-alkyl, $C_2$-$C_6$-alkenyl and $C_2$-$C_6$-alkynyl, $C_3$-$C_6$-cycloalkyl, $C_5$-$C_6$-cycloalkenyl, $C_1$-$C_6$-alkoxy, CN, $NO_2$, or $S(O)_n R^b$, wherein the C-atoms may be unsubstituted, or partially or fully substituted by $R^a$;
  $R^a$ is halogen, CN, $NO_2$, $C_1$-$C_2$-alkyl, $C_1$-$C_2$-haloalkyl, $C_1$-$C_4$-alkoxy, $C_1$-$C_2$-haloalkoxy, or $S(O)_n R^b$, wherein n is 0, 1, or 2;
  $R^b$ is hydrogen, $C_1$-$C_2$-alkyl, $C_1$-$C_2$-haloalkyl, $C_3$-$C_6$-cycloalkyl, or $C_1$-$C_4$-alkoxy,
$R^4$ is $C_1$-$C_4$-alkyl, or a group mentioned for $R^3$;
$R^5$ is H, or a group mentioned for $R^4$;
$R^3$ and $R^4$ may together form a three- to six-membered carbo- or heterocycle, which may contain 1 or 2 heteroatoms selected from N—$R^c$, O, and S, wherein S may be oxidised, which carbo- or heterocycle may be substituted by $R^a$;
  $R^c$ is hydrogen, $C_1$-$C_2$-alkyl, $C_1$-$C_2$-haloalkyl, $C_1$-$C_2$-alkylcarbonyl, or $C_1$-$C_2$-alkoxycarbonyl;
and the stereoisomers, salts, tautomers and N-oxides thereof.

Moreover, the invention relates to processes and intermediates for preparing the pyrazoles of formula I, and also to active compound combinations comprising them, to compositions comprising them and to their use for combating invertebrate pests. Furthermore, the invention relates to methods of applying such compounds.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

WO 2009/027393, WO 2010/034737, WO 2010/034738, and WO 2010/112177 describe derivatives of N-arylamides, derived from pyrazole carboxylic acids. These compounds are mentioned to be useful for combating invertebrate pests.

Invertebrate pests and in particular arthropods and nematodes destroy growing and harvested crops and attack wooden dwelling and commercial structures, thereby causing large economic loss to the food supply and to property. There is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control pests, such as insects.

It has been found that these objectives can be achieved by compounds of formula I, as defined in the outset, and by their stereoisomers, salts, tautomers and N-oxides, in particular their agriculturally acceptable salts.

One embodiment of the invention relates to compounds of formula I, wherein U is CH. These compounds correspond to the formula I.A.

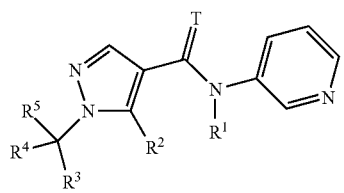

I.A

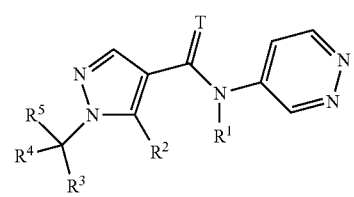

I.B

A further embodiment of the invention relates to compounds of formula I, wherein U is N. These compounds correspond to the formula I.B.

The compounds according to the invention can be prepared analogously to the synthesis routes described in WO 2009/027393 and WO 2010/034737 according to standard processes of organic chemistry, for example according to the following synthesis route:

Compounds of formula I, wherein T is O (formula I.1), can be prepared e.g. by reacting activated pyrazole carboxylic acid derivative II with a 3-aminopyridine, or 4-aminopyridazine of formula III (e.g. Houben-Weyl: "Methoden der organ. Chemie" [Methods of Organic Chemistry], Georg-Thieme-Verlag, Stuttgart, New York 1985, Volume E5, pp. 941-1045).

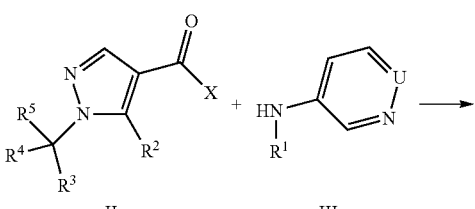

II   III

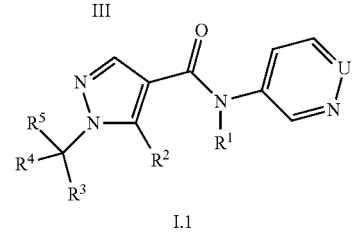

I.1

Activated pyrazole carboxylic acid derivatives II are preferably halides, activated esters, anhydrides, azides, for example chlorides, fluorides, bromides, para-nitrophenyl esters, pentafluorophenyl esters, N-hydroxysuccinimides, hydroxybenzotriazol-1-yl esters.

In formulae II and III, the radicals have the meanings mentioned above for formula I and in particular the meanings mentioned as being preferred, X is a suitable leaving group such as halogen, N3, p-nitrophenoxy or pentafluorophenoxy and the like.

Compounds of formula I.1 wherein $R^1$ is different from hydrogen can also be prepared by alkylating the amides I.1, in which $R^1$ is hydrogen, using suitable alkylating agents in the presence of bases. The alkylation can be effected under standard conditions known from literature.

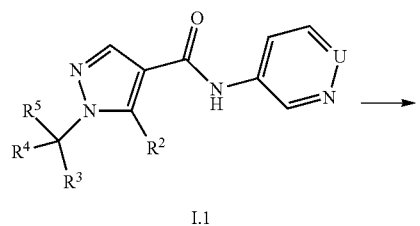

I.1

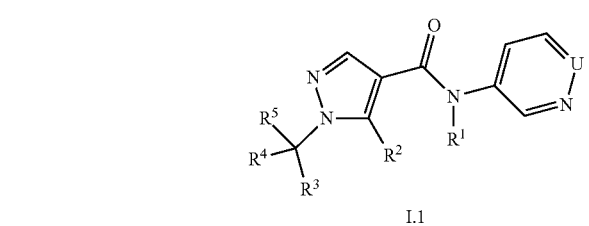

I.1

($R^1$ = H)

Formula I compounds may be present in two isomeric forms, and formula I.B compounds in three isomeric forms, hence formula I encompasses both tautomers T-A and T-B, and for formula I.B also T-C:

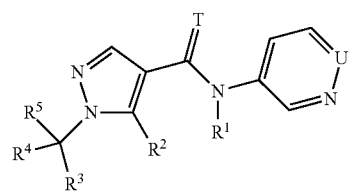

T-A

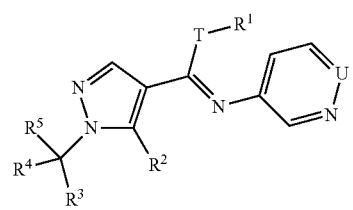

T-B

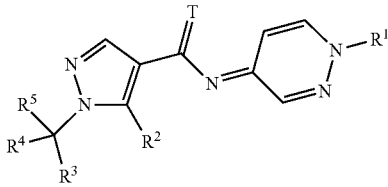

T-C

For reasons of clarity it is referred to isomer T-A only throughout the specification, but its description embraces disclosure of the other isomers as well. Isomer T-C can be obtained by alkylation of compounds I.B.1 wherein $R^1$ is hydrogen. The reaction can be performed by analogy to known N-alkylation of pyridazines. N-Alkylation of Pyridazines is known in literature and can be found in e.g.: J. Chem. Soc., Perkin Trans. Vol. 1, p. 401 (1988), and J. Org. Chem. Vol. 46, p. 2467 (1981).

I.B.1

($R^1$ = H)

Compounds of the formula I, wherein T is S (formula I.2), can be prepared e.g. by reacting compounds of formula I.1 with 2,4-bis(4-methoxyphenyl)-1,3,2,4-dithiadiphosphetane-2,4-di-sulfide or $PS_5$ according to the method described in Synthesis 2003, p. 1929.

The compounds II and III are known in the art or are commercially available or can be prepared by methods known from the literature (cf. WO 05/040169; WO 08/074,824; Journal of Fluorine chemistry 132(11), p. 995 (2011)).

N-oxides of the compounds of formula I, can be prepared by oxidation of compounds I according to standard methods of preparing heteroaromatic N-oxides, e.g. by the method described in Journal of Organometallic Chemistry 1989, 370, 17-31.

If individual compounds cannot be prepared via the above-described routes, they can be prepared by derivatization of other compounds I or by customary modifications of the synthesis routes described. For example, in individual cases, certain compounds I can advantageously be prepared from other compounds I by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The radicals attached to the backbone of formula I may contain one or more centers of chirality. In this case the formula I are present in the form of different enantiomers or diastereomers, depending on the substituents. The present invention relates to every possible stereoisomer of the formula I, i.e. to single enantiomers or diastereomers, as well as to mixtures thereof.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

Salts of the compounds of the formula I are preferably agriculturally acceptable salts. They can be formed in a customary manner, e.g. by reacting the compound with an acid of the anion in question if the compound of formula I has a basic functionality.

Agriculturally useful salts of the compounds of formula I encompass especially the acid addition salts of those acids whose cations and anions, respectively, have no adverse effect on the pesticidal action of the compounds of formula I.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formula I with an acid of the corresponding anion, preferably of hydrochloric acid, hydrobromic acid, sulfuric acid, phosphoric acid or nitric acid.

The term "N-oxide" includes any compound of formula I which has at least one tertiary nitrogen atom that is oxidized to an N-oxide moiety.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 6 carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkoxy, haloalkylthio, haloalkylcarbonyl, haloalkylsulfonyl and haloalkylsulfinyl, denotes in each case a straight-chain or branched alkyl group having usually from 1 to 6 carbon atoms, frequently from 1 to 4 carbon atoms, wherein the hydrogen atoms of this group are partially or totally replaced with halogen atoms. Preferred haloalkyl moieties are selected from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "cycloalkyl" as used herein and in the cycloalkyl moieties of cycloalkoxy and cycloalkylmethyl denotes in each case a monocyclic cycloaliphatic radical having usually from 3 to 6 carbon atoms, such as cyclopropyl, cyclobutyl, cyclopentyl, and cyclohexyl.

The term "alkenyl" as used herein denotes in each case a singly unsaturated hydrocarbon radical having usually 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkoxyalkyl" as used herein refers to alkyl usually comprising 1 to 2 carbon atoms, wherein 1 carbon atom carries an alkoxy radical usually comprising 1 or 2 carbon atoms as defined above. Examples are $CH_2OCH_3$, $CH_2$—$OC_2H_5$, 2-(methoxy)ethyl, and 2-(ethoxy)ethyl.

The term "heterocyclyl" includes in general 5-, or 6-membered, in particular 6-membered monocyclic heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

Examples of 5-, or 6-membered heterocyclic radicals comprise saturated or unsaturated, non-aromatic heterocyclic rings, such as oxiranyl, oxetanyl, thietanyl, thietanyl-5-oxid (S-oxothietanyl), thietanyl-5-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetra-hydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

With respect to the variables, the particularly preferred embodiments of the intermediates correspond to those of the groups of the formula I.

In a particular embodiment, the variables of the compounds of the formula I have the following meanings, these meanings, both on their own and in combination with one another, being particular embodiments of the compounds of the formula I:

In one preferred embodiment of the compounds of the formula I, U is CH. These compounds correspond to the formula I.A.

In a further embodiment of the compounds of the formula I, U is N. These compounds correspond to the formula I.B.

In a first preferred embodiment of formula I, T is O. These compounds correspond to the formula I.1.

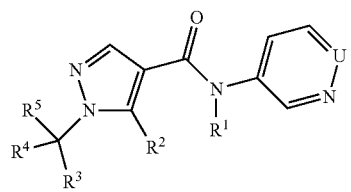

I.1

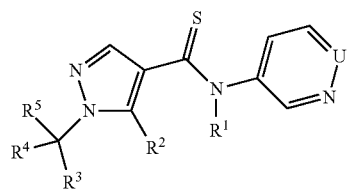

I.2

In another embodiment of formula I, T is S. These compounds correspond to the formula I.2.

In a first embodiment, $R^1$ is H.

In a further embodiment, $R^1$ is $C_1$-$C_2$-alkyl, preferably $CH_3$.

In a further embodiment, $R^1$ is $CH_2CH_3$.

In a further embodiment, $R^1$ is $C_1$-$C_2$-alkoxy-$C_1$-$C_2$-alkyl, preferably $C_1$-$C_2$-alkoxy-methyl, particularly $CH_2OCH_3$.

In a first embodiment, $R^2$ is $CH_3$.

In a further embodiment, $R^2$ is halomethyl, preferably fluoromethyl, particularly $CHF_2$, or $CF_3$.

In a first preferred embodiment, $R^3$ is $C_2$-$C_6$-alkyl, preferably $C_2$-$C_4$-alkyl, particularly $CH_2CH_3$, or $C(CH_3)_3$.

In another preferred embodiment, $R^3$ is $C_1$-$C_6$-haloalkyl, preferably $C_1$-$C_2$-alkyl, more preferred halomethyl, such as $CHF_2$, or $CF_3$, particularly $CF_3$.

In another preferred embodiment, $R^3$ is $C_1$-$C_2$-alkoxy-$C_1$-$C_2$-alkyl, preferably $C_1$-$C_2$-alkoxy-methyl, particularly $CH_2OCH_3$.

In another preferred embodiment, $R^3$ is $C_3$-$C_6$-cycloalkyl, preferably cyclopropyl, being unsubstituted or substituted, preferably by halogen or cyano. Substituents are preferably in 1- or in 2,2-position.

In a first preferred embodiment $R^4$ is $C_1$-$C_4$-alkyl, preferably $C_1$-$C_2$-alkyl, particularly $CH_3$.

In another preferred embodiment $R^4$ is $C_1$-$C_6$-haloalkyl, preferably $C_1$-$C_2$-alkyl, particularly halomethyl, such as $CF_3$.

In a further embodiment $R^4$ is $C_3$-$C_6$-cycloalkyl, preferably cyclopropyl, which may be substituted, preferably by halogen or cyano. Substituents are preferably in 1- or in 2,2-position.

In a first preferred embodiment, $R^5$ is hydrogen.

In another preferred embodiment, $R^5$ is CN or $NO_2$, preferably CN.

In another preferred embodiment, $R^5$ is $C_1$-$C_4$-alkyl, preferably $C_1$-$C_2$-alkyl, particularly $CH_3$.

In another embodiment, $R^3$ and $R^4$ form a five- or six-membered saturated carbocycle, such as cyclopentyl or cyclohexyl, being unsubstituted or substituted by one or more groups $R^a$. Such $R^a$ groups are preferably halogen, cyano, or halomethyl.

In another embodiment, $R^3$ and $R^4$ form a five- or six-membered saturated heterocycle, which contains 1 or 2, preferably 1, heteroatoms selected from N—$R^c$, O, and S, wherein S may be oxidised, the heterocycle being unsubstituted or substituted by one or more groups $R^d$.

$R^c$ preferably denotes $C_1$-$C_2$-alkyl, particularly $CH_3$, or $C_1$-$C_2$-alkylcarbonyl, particularly acetyl.

The heterocyclus is preferably unsubstituted.

In one embodiment, the heterocyclus being formed by $R^3$ and $R^4$ represents a group H:

H wherein G represents N—$R^c$, O, S, S(=O), or $SO_2$, and # denotes the bond to the pyrazole moiety.

Another embodiment relates to compounds of formula I excluding the racemic compounds, wherein T is O, $R^1$ is H, $C_1$-$C_2$-alkyl, or $CH_2OCH_3$, $R^2$ is $CH_3$, $CHF_2$, or $CF_3$, $R^3$ is $CF_3$, or cyclopropyl, $R^4$ is $CH_3$, and $R^5$ is H.

In particular with a view to their use, preference is given to the compounds of the formula I compiled in the tables below, which compounds correspond to the formula I.1. Each of the groups mentioned for a substituent in the tables is furthermore per se, independently of the combination in which it is mentioned, a particularly preferred aspect of the substituent in question.

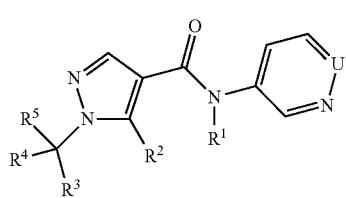

I.1

Table 1

Compounds of the formula I.1 in which U is CH, $R^1$ is H, $R^2$ is $CH_3$ and the combination of $R^3$, $R^4$ and $R^5$ for a compound corresponds in each case to one row of Table A Table 2

Compounds of the formula I.1 in which U is N, $R^1$ is H, $R^2$ is $CH_3$ and the combination of $R^3$, $R^4$ and $R^5$ for a compound corresponds in each case to one row of Table A Table 3

Compounds of the formula I.1 in which U is CH, $R^1$ is H, $R^2$ is $CHF_2$ and the combination of $R^3$, $R^4$ and $R^5$ for a compound corresponds in each case to one row of Table A Table 4

Compounds of the formula I.1 in which U is N, $R^1$ is H, $R^2$ is $CHF_2$ and the combination of $R^3$, $R^4$ and $R^5$ for a compound corresponds in each case to one row of Table A Table 5

Compounds of the formula I.1 in which U is CH, $R^1$ is H, $R^2$ is $CF_3$ and the combination of $R^3$, $R^4$ and $R^5$ for a compound corresponds in each case to one row of Table A Table 6
Compounds of the formula I.1 in which U is N, $R^1$ is H, $R^2$ is $CF_3$ and the combination of $R^3$, $R^4$ and $R^5$ for a compound corresponds in each case to one row of Table A Table 7
Compounds of the formula I.1 in which U is CH, $R^1$ and $R^2$ are $CH_3$ and the combination of $R^3$, $R^4$ and $R^5$ for a compound corresponds in each case to one row of Table A Table 8
Compounds of the formula I.1 in which U is N, $R^1$ and $R^2$ are $CH_3$ and the combination of $R^3$, $R^4$ and $R^5$ for a compound corresponds in each case to one row of Table A Table 9
Compounds of the formula I.1 in which U is CH, $R^1$ is $CH_3$, $R^2$ is $CHF_2$ and the combination of $R^3$, $R^4$ and $R^5$ for a compound corresponds in each case to one row of Table A Table 10
Compounds of the formula I.1 in which U is N, $R^1$ is $CH_3$, $R^2$ is $CHF_2$ and the combination of $R^3$, $R^4$ and $R^5$ for a compound corresponds in each case to one row of Table A Table 11
Compounds of the formula I.1 in which U is CH, $R^1$ is $CH_3$, $R^2$ is $CF_3$ and the combination of $R^3$, $R^4$ and $R^5$ for a compound corresponds in each case to one row of Table A Table 12
Compounds of the formula I.1 in which U is N, $R^1$ is $CH_3$, $R^2$ is $CF_3$ and the combination of $R^3$, $R^4$ and $R^5$ for a compound corresponds in each case to one row of Table A Table 13
Compounds of the formula I.1 in which U is CH, $R^1$ is $CH_2CH_3$, $R^2$ is $CH_3$ and the combination of $R^3$, $R^4$ and $R^5$ for a compound corresponds in each case to one row of Table A Table 14
Compounds of the formula I.1 in which U is N, $R^1$ is $CH_2CH_3$, $R^2$ is $CH_3$ and the combination of $R^3$, $R^4$ and $R^5$ for a compound corresponds in each case to one row of Table A Table 15
Compounds of the formula I.1 in which U is CH, $R^1$ is $CH_2CH_3$, $R^2$ is $CHF_2$ and the combination of $R^3$, $R^4$ and $R^5$ for a compound corresponds in each case to one row of Table A Table 16
Compounds of the formula I.1 in which U is N, $R^1$ is $CH_2CH_3$, $R^2$ is $CHF_2$ and the combination of $R^3$, $R^4$ and $R^5$ for a compound corresponds in each case to one row of Table A Table 17
Compounds of the formula I.1 in which U is CH, $R^1$ is $CH_2CH_3$, $R^2$ is $CF_3$ and the combination of $R^3$, $R^4$ and $R^5$ for a compound corresponds in each case to one row of Table A Table 18
Compounds of the formula I.1 in which U is N, $R^1$ is $CH_2CH_3$, $R^2$ is $CF_3$ and the combination of $R^3$, $R^4$ and $R^5$ for a compound corresponds in each case to one row of Table A Table 19
Compounds of the formula I.1 in which U is CH, $R^1$ is $CH_2OCH_3$, $R^2$ is $CH_3$ and the combination of $R^3$, $R^4$ and $R^5$ for a compound corresponds in each case to one row of Table A Table 20
Compounds of the formula I.1 in which U is N, $R^1$ is $CH_2OCH_3$, $R^2$ is $CH_3$ and the combination of $R^3$, $R^4$ and $R^5$ for a compound corresponds in each case to one row of Table A Table 21
Compounds of the formula I.1 in which U is CH, $R^1$ is $CH_2OCH_3$, $R^2$ is $CHF_2$ and the combination of $R^3$, $R^4$ and $R^5$ for a compound corresponds in each case to one row of Table A Table 22
Compounds of the formula I.1 in which U is N, $R^1$ is $CH_2OCH_3$, $R^2$ is $CHF_2$ and the combination of $R^3$, $R^4$ and $R^5$ for a compound corresponds in each case to one row of Table A Table 23
Compounds of the formula I.1 in which U is CH, $R^1$ is $CH_2OCH_3$, $R^2$ is $CF_3$ and the combination of $R^3$, $R^4$ and $R^5$ for a compound corresponds in each case to one row of Table A Table 24
Compounds of the formula I.1 in which U is N, $R^1$ is $CH_2OCH_3$, $R^2$ is $CF_3$ and the combination of $R^3$, $R^4$ and $R^5$ for a compound corresponds in each case to one row of Table A Table 25
Compounds of the formula I.1 in which U is CH, $R^1$ is $CH_2OCH_2CH_3$, $R^2$ is $CH_3$ and the combination of $R^3$, $R^4$ and $R^5$ for a compound corresponds in each case to one row of Table A Table 26
Compounds of the formula I.1 in which U is N, $R^1$ is $CH_2OCH_2CH_3$, $R^2$ is $CH_3$ and the combination of $R^3$, $R^4$ and $R^5$ for a compound corresponds in each case to one row of Table A Table 27
Compounds of the formula I.1 in which U is CH, $R^1$ is $CH_2OCH_2CH_3$, $R^2$ is $CHF_2$ and the combination of $R^3$, $R^4$ and $R^5$ for a compound corresponds in each case to one row of Table A Table 28
Compounds of the formula I.1 in which U is N, $R^1$ is $CH_2OCH_2CH_3$, $R^2$ is $CHF_2$ and the combination of $R^3$, $R^4$ and $R^5$ for a compound corresponds in each case to one row of Table A Table 29
Compounds of the formula I.1 in which U is CH, $R^1$ is $CH_2OCH_2CH_3$, $R^2$ is $CF_3$ and the combination of $R^3$, $R^4$ and $R^5$ for a compound corresponds in each case to one row of Table A Table 30
Compounds of the formula I.1 in which U is N, $R^1$ is $CH_2OCH_2CH_3$, $R^2$ is $CF_3$ and the combination of $R^3$, $R^4$ and $R^5$ for a compound corresponds in each case to one row of Table A

TABLE A

| No. | $R^3$ | $R^4$ | $R^5$ |
|---|---|---|---|
| A-1 | CN | $CH_3$ | H |
| A-2 | $CH_2CH_3$ | $CH_3$ | H |
| A-3 | $C(CH_3)_3$ | $CH_3$ | H |
| A-4 | $CHF_2$ | $CH_3$ | H |
| A-5 | $CF_3$ | $CH_3$ | H |
| A-6 | $CH_2OCH_3$ | $CH_3$ | H |
| A-7 | $c$-$C_3H_5$ | $CH_3$ | H |
| A-8 | 1-F-c-$C_3H_4$ | $CH_3$ | H |
| A-9 | 1-CN-c-$C_3H_4$ | $CH_3$ | H |

TABLE A-continued

| No. | R³ | R⁴ | R⁵ |
|---|---|---|---|
| A-10 | 2,2-F₂-c-C₃H₃ | CH₃ | H |
| A-11 | 2,2-Cl₂-c-C₃H₃ | CH₃ | H |
| A-12 | c-C₄H₇ | CH₃ | H |
| A-13 | c-C₅H₉ | CH₃ | H |
| A-14 | c-C₆H₁₁ | CH₃ | H |
| A-15 | 1-CN-c-C₆H₁₀ | CH₃ | H |
| A-16 | 1-CH₃-c-C₆H₁₀ | CH₃ | H |
| A-17 | 1-CF₃-c-C₆H₁₀ | CH₃ | H |
| A-18 | CN | CH₂CH₃ | H |
| A-19 | CH₂CH₃ | CH₂CH₃ | H |
| A-20 | C(CH₃)₃ | CH₂CH₃ | H |
| A-21 | CHF₂ | CH₂CH₃ | H |
| A-22 | CF₃ | CH₂CH₃ | H |
| A-23 | CH₂OCH₃ | CH₂CH₃ | H |
| A-24 | c-C₃H₅ | CH₂CH₃ | H |
| A-25 | 1-F-c-C₃H₄ | CH₂CH₃ | H |
| A-26 | 1-CN-c-C₃H₄ | CH₂CH₃ | H |
| A-27 | 2,2-F₂-c-C₃H₃ | CH₂CH₃ | H |
| A-28 | 2,2-Cl₂-c-C₃H₃ | CH₂CH₃ | H |
| A-29 | c-C₄H₇ | CH₂CH₃ | H |
| A-30 | c-C₅H₉ | CH₂CH₃ | H |
| A-31 | c-C₆H₁₁ | CH₂CH₃ | H |
| A-32 | 1-CN-c-C₆H₁₀ | CH₂CH₃ | H |
| A-33 | 1-CH₃-c-C₆H₁₀ | CH₂CH₃ | H |
| A-34 | 1-CF₃-c-C₆H₁₀ | CH₂CH₃ | H |
| A-35 | CN | CF₃ | H |
| A-36 | CH₂CH₃ | CF₃ | H |
| A-37 | C(CH₃)₃ | CF₃ | H |
| A-38 | CHF₂ | CF₃ | H |
| A-39 | CF₃ | CF₃ | H |
| A-40 | CH₂OCH₃ | CF₃ | H |
| A-41 | c-C₃H₅ | CF₃ | H |
| A-42 | 1-F-c-C₃H₄ | CF₃ | H |
| A-43 | 1-CN-c-C₃H₄ | CF₃ | H |
| A-44 | 2,2-F₂-c-C₃H₃ | CF₃ | H |
| A-45 | 2,2-Cl₂-c-C₃H₃ | CF₃ | H |
| A-46 | c-C₄H₇ | CF₃ | H |
| A-47 | c-C₅H₉ | CF₃ | H |
| A-48 | c-C₆H₁₁ | CF₃ | H |
| A-49 | 1-CN-c-C₆H₁₀ | CF₃ | H |
| A-50 | 1-CH₃-c-C₆H₁₀ | CF₃ | H |
| A-51 | 1-CF₃-c-C₆H₁₀ | CF₃ | H |
| A-52 | CN | CH₃ | CH₃ |
| A-53 | CH₂CH₃ | CH₃ | CH₃ |
| A-54 | C(CH₃)₃ | CH₃ | CH₃ |
| A-55 | CHF₂ | CH₃ | CH₃ |
| A-56 | CF₃ | CH₃ | CH₃ |
| A-57 | CH₂OCH₃ | CH₃ | CH₃ |
| A-58 | c-C₃H₅ | CH₃ | CH₃ |
| A-59 | 1-F-c-C₃H₄ | CH₃ | CH₃ |
| A-60 | 1-CN-c-C₃H₄ | CH₃ | CH₃ |
| A-61 | 2,2-F₂-c-C₃H₃ | CH₃ | CH₃ |
| A-62 | 2,2-Cl₂-c-C₃H₃ | CH₃ | CH₃ |
| A-63 | c-C₄H₇ | CH₃ | CH₃ |
| A-64 | c-C₅H₉ | CH₃ | CH₃ |
| A-65 | c-C₆H₁₁ | CH₃ | CH₃ |
| A-66 | 1-CN-c-C₆H₁₀ | CH₃ | CH₃ |
| A-67 | 1-CH₃-c-C₆H₁₀ | CH₃ | CH₃ |
| A-68 | 1-CF₃-c-C₆H₁₀ | CH₃ | CH₃ |
| A-69 | CN | CH₂CH₃ | CH₃ |
| A-70 | CH₂CH₃ | CH₂CH₃ | CH₃ |
| A-71 | C(CH₃)₃ | CH₂CH₃ | CH₃ |
| A-72 | CHF₂ | CH₂CH₃ | CH₃ |
| A-73 | CF₃ | CH₂CH₃ | CH₃ |
| A-74 | CH₂OCH₃ | CH₂CH₃ | CH₃ |
| A-75 | c-C₃H₅ | CH₂CH₃ | CH₃ |
| A-76 | 1-F-c-C₃H₄ | CH₂CH₃ | CH₃ |
| A-77 | 1-CN-c-C₃H₄ | CH₂CH₃ | CH₃ |
| A-78 | 2,2-F₂-c-C₃H₃ | CH₂CH₃ | CH₃ |
| A-79 | 2,2-Cl₂-c-C₃H₃ | CH₂CH₃ | CH₃ |
| A-80 | c-C₄H₇ | CH₂CH₃ | CH₃ |
| A-81 | c-C₅H₉ | CH₂CH₃ | CH₃ |
| A-82 | c-C₆H₁₁ | CH₂CH₃ | CH₃ |
| A-83 | 1-CN-c-C₆H₁₀ | CH₂CH₃ | CH₃ |
| A-84 | 1-CH₃-c-C₆H₁₀ | CH₂CH₃ | CH₃ |
| A-85 | 1-CF₃-c-C₆H₁₀ | CH₂CH₃ | CH₃ |
| A-86 | CN | CF₃ | CH₃ |
| A-87 | CH₂CH₃ | CF₃ | CH₃ |
| A-88 | C(CH₃)₃ | CF₃ | CH₃ |
| A-89 | CHF₂ | CF₃ | CH₃ |
| A-90 | CF₃ | CF₃ | CH₃ |
| A-91 | CH₂OCH₃ | CF₃ | CH₃ |
| A-92 | c-C₃H₅ | CF₃ | CH₃ |
| A-93 | 1-F-c-C₃H₄ | CF₃ | CH₃ |
| A-94 | 1-CN-c-C₃H₄ | CF₃ | CH₃ |
| A-95 | 2,2-F₂-c-C₃H₃ | CF₃ | CH₃ |
| A-96 | 2,2-Cl₂-c-C₃H₃ | CF₃ | CH₃ |
| A-97 | c-C₄H₇ | CF₃ | CH₃ |
| A-98 | c-C₅H₉ | CF₃ | CH₃ |
| A-99 | c-C₆H₁₁ | CF₃ | CH₃ |
| A-100 | 1-CN-c-C₆H₁₀ | CF₃ | CH₃ |
| A-101 | 1-CH₃-c-C₆H₁₀ | CF₃ | CH₃ |
| A-102 | 1-CF₃-c-C₆H₁₀ | CF₃ | CH₃ |
| A-103 | c-C₃H₅ | CH₂CH₃ | CF₃ |
| A-104 | 1-F-c-C₃H₄ | CH₂CH₃ | CF₃ |
| A-105 | 1-CN-c-C₃H₄ | CH₂CH₃ | CF₃ |
| A-106 | 2,2-F₂-c-C₃H₃ | CH₂CH₃ | CF₃ |
| A-107 | 2,2-Cl₂-c-C₃H₃ | CH₂CH₃ | CF₃ |
| A-108 | c-C₄H₇ | CH₂CH₃ | CF₃ |
| A-109 | c-C₅H₉ | CH₂CH₃ | CF₃ |
| A-110 | c-C₆H₁₁ | CH₂CH₃ | CF₃ |
| A-111 | 1-CN-c-C₆H₁₀ | CH₂CH₃ | CF₃ |
| A-112 | 1-CH₃-c-C₆H₁₀ | CH₂CH₃ | CF₃ |
| A-113 | 1-CF₃-c-C₆H₁₀ | CH₂CH₃ | CF₃ |
| A-114 | CN | CF₃ | CF₃ |
| A-115 | CH₂CH₃ | CF₃ | CF₃ |
| A-116 | C(CH₃)₃ | CF₃ | CF₃ |
| A-117 | CHF₂ | CF₃ | CF₃ |
| A-118 | CF₃ | CF₃ | CF₃ |
| A-119 | CH₂OCH₃ | CF₃ | CF₃ |
| A-120 | c-C₃H₅ | CF₃ | CF₃ |
| A-121 | 1-F-c-C₃H₄ | CF₃ | CF₃ |
| A-122 | 1-CN-c-C₃H₄ | CF₃ | CF₃ |
| A-123 | 2,2-F₂-c-C₃H₃ | CF₃ | CF₃ |
| A-124 | 2,2-Cl₂-c-C₃H₃ | CF₃ | CF₃ |
| A-125 | c-C₄H₇ | CF₃ | CF₃ |
| A-126 | c-C₅H₉ | CF₃ | CF₃ |
| A-127 | c-C₆H₁₁ | CF₃ | CF₃ |
| A-128 | 1-CN-c-C₆H₁₀ | CF₃ | CF₃ |
| A-129 | 1-CH₃-c-C₆H₁₀ | CF₃ | CF₃ |
| A-130 | 1-CF₃-c-C₆H₁₀ | CF₃ | CF₃ |
| A-131 | CN | CH₃ | CN |
| A-132 | CH₂CH₃ | CH₃ | CN |
| A-133 | C(CH₃)₃ | CH₃ | CN |
| A-134 | CHF₂ | CH₃ | CN |
| A-135 | CF₃ | CH₃ | CN |
| A-136 | CH₂OCH₃ | CH₃ | CN |
| A-137 | c-C₃H₅ | CH₃ | CN |
| A-138 | 1-F-c-C₃H₄ | CH₃ | CN |
| A-139 | 1-CN-c-C₃H₄ | CH₃ | CN |
| A-140 | 2,2-F₂-c-C₃H₃ | CH₃ | CN |
| A-141 | 2,2-Cl₂-c-C₃H₃ | CH₃ | CN |
| A-142 | c-C₄H₇ | CH₃ | CN |
| A-143 | c-C₅H₉ | CH₃ | CN |
| A-144 | c-C₆H₁₁ | CH₃ | CN |
| A-145 | 1-CN-c-C₆H₁₀ | CH₃ | CN |
| A-146 | 1-CH₃-c-C₆H₁₀ | CH₃ | CN |
| A-147 | 1-CF₃-c-C₆H₁₀ | CH₃ | CN |
| A-148 | CN | CH₂CH₃ | CN |
| A-149 | CH₂CH₃ | CH₂CH₃ | CN |
| A-150 | C(CH₃)₃ | CH₂CH₃ | CN |
| A-151 | CHF₂ | CH₂CH₃ | CN |
| A-152 | CF₃ | CH₂CH₃ | CN |
| A-153 | CH₂OCH₃ | CH₂CH₃ | CN |
| A-154 | c-C₃H₅ | CH₂CH₃ | CN |
| A-155 | 1-F-c-C₃H₄ | CH₂CH₃ | CN |
| A-156 | 1-CN-c-C₃H₄ | CH₂CH₃ | CN |
| A-157 | 2,2-F₂-c-C₃H₃ | CH₂CH₃ | CN |
| A-158 | 2,2-Cl₂-c-C₃H₃ | CH₂CH₃ | CN |
| A-159 | c-C₄H₇ | CH₂CH₃ | CN |
| A-160 | c-C₅H₉ | CH₂CH₃ | CN |
| A-161 | c-C₆H₁₁ | CH₂CH₃ | CN |
| A-162 | 1-CN-c-C₆H₁₀ | CH₂CH₃ | CN |
| A-163 | 1-CH₃-c-C₆H₁₀ | CH₂CH₃ | CN |
| A-164 | 1-CF₃-c-C₆H₁₀ | CH₂CH₃ | CN |
| A-165 | CN | CF₃ | CN |

TABLE A-continued

| No. | R³ | R⁴ | R⁵ |
|---|---|---|---|
| A-166 | $CH_2CH_3$ | $CF_3$ | CN |
| A-167 | $C(CH_3)_3$ | $CF_3$ | CN |
| A-168 | $CHF_2$ | $CF_3$ | CN |
| A-169 | $CF_3$ | $CF_3$ | CN |
| A-170 | $CH_2OCH_3$ | $CF_3$ | CN |
| A-171 | $c\text{-}C_3H_5$ | $CF_3$ | CN |
| A-172 | $1\text{-}F\text{-}c\text{-}C_3H_4$ | $CF_3$ | CN |
| A-173 | $1\text{-}CN\text{-}c\text{-}C_3H_4$ | $CF_3$ | CN |
| A-174 | $2,2\text{-}F_2\text{-}c\text{-}C_3H_3$ | $CF_3$ | CN |
| A-175 | $2,2\text{-}Cl_2\text{-}c\text{-}C_3H_3$ | $CF_3$ | CN |
| A-176 | $c\text{-}C_4H_7$ | $CF_3$ | CN |
| A-177 | $c\text{-}C_5H_9$ | $CF_3$ | CN |
| A-178 | $c\text{-}C_6H_{11}$ | $CF_3$ | CN |
| A-179 | $1\text{-}CN\text{-}c\text{-}C_6H_{10}$ | $CF_3$ | CN |
| A-180 | $1\text{-}CH_3\text{-}c\text{-}C_6H_{10}$ | $CF_3$ | CN |
| A-181 | $1\text{-}CF_3\text{-}c\text{-}C_6H_{10}$ | $CF_3$ | CN |
| A-182 |  | $-CH_2CH_2-$ | H |
| A-183 |  | $-CH_2CF_2-$ | H |
| A-184 |  | $-CH_2CCl_2-$ | H |
| A-185 |  | $-CH_2CH_2-CH_2-$ | H |
| A-186 |  | $-CH_2CH_2-CH_2-CH_2-$ | H |
| A-187 |  | $-CH_2CH_2-CH_2-CH_2CH_2-$ | H |
| A-188 |  | $-CH_2CH_2-O-CH_2CH_2-$ | H |
| A-189 |  | $-CH_2CH_2-N(CH_3)-CH_2CH_2-$ | H |
| A-190 |  | $-CH_2CH_2N(COCH_3)CH_2CH_2-$ | H |
| A-191 |  | $-CH_2CH_2-$ | $CF_3$ |
| A-192 |  | $-CH_2CF_2-$ | $CF_3$ |
| A-193 |  | $-CH_2CCl_2-$ | $CF_3$ |
| A-194 |  | $-CH_2CH_2-CH_2-$ | $CF_3$ |
| A-195 |  | $-CH_2CH_2-CH_2-CH_2-$ | $CF_3$ |
| A-196 |  | $-CH_2CH_2-CH_2-CH_2CH_2-$ | $CF_3$ |
| A-197 |  | $-CH_2CH_2-O-CH_2CH_2-$ | $CF_3$ |
| A-198 |  | $-CH_2CH_2-N(CH_3)-CH_2CH_2-$ | $CF_3$ |
| A-199 |  | $-CH_2CH_2N(COCH_3)CH_2CH_2-$ | $CF_3$ |
| A-200 |  | $-CH_2CH_2-$ | CN |
| A-201 |  | $-CH_2CF_2-$ | CN |
| A-202 |  | $-CH_2CCl_2-$ | CN |
| A-203 |  | $-CH_2CH_2-CH_2-$ | CN |
| A-204 |  | $-CH_2CH_2-CH_2-CH_2-$ | CN |
| A-205 |  | $-CH_2CH_2-CH_2-CH_2CH_2-$ | CN |
| A-206 |  | $-CH_2CH_2-O-CH_2CH_2-$ | CN |
| A-207 |  | $-CH_2CH_2-N(CH_3)-CH_2CH_2-$ | CN |
| A-208 |  | $-CH_2CH_2N(COCH_3)CH_2CH_2-$ | CN |

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above.

The present invention also relates to a method for protecting growing plants from attack or infestation by invertebrate pests, preferably of the group of insects, which method comprises contacting a plant, or soil or water in which the plant is growing or may grow, with a pesticidally effective amount of at least one compound according to the invention including a stereoisomer, salt, tautomer or N-oxide thereof or a composition according to the invention.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The compounds of the present invention, including their salts, stereoisomers and tautomers, are in particular suitable for efficiently controlling arthropodal pests such as arachnids, myriapedes and insects as well as nematodes, especially insects. They are especially suitable for efficiently combating or controlling the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochle-*

*ariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schnideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of the present invention, including their salts, stereoisomers and tautomers, are particularly useful for controlling insects, preferably sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Thrips oryzae, Thrips palmi* and *Thrips tabaci.*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura bras-*

*sicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola*, and *Tabanus similis, Tipula oleracea*, and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii.*

The compounds of the present invention, including their salts, stereoisomers and tautomers, are particularly useful for controlling insects of the orders Hemiptera and Thysanoptera.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or salt as well as individual tautomers or mixtures of tautomers.

The compounds of the present invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineers Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998, for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
  solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
  carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal.

Suitable thickeners are compounds which confer a pseudo-plastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations, i.e. the compositions according to the invention, comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The following are examples of formulations:
1. Products for dilution with water. For seed treatment purposes, such products may be applied to the seed diluted or undiluted.

A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the methods and uses of this invention, the compounds according to the invention may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphosmethyl, chlorethoxyfos, chlorfenvinphos, chlormephos, chlorpyrifos, chlorpyrifos-methyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemetonmethyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultapsodium and AKD1022.

M.6. GABA gated chloride channel antagonist compounds: chlordane, endosulfan, gammaHCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1);

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethyl-carbamoyl)-methyl]-benzamide (M22.3), 4-[5-(3,5-Dichloro-phenyl)-5-trifluoromethyl-4,5-dihydro-isoxazol-3-yl]naphthalene-1-carboxylic acid [(2,2,2-trifluoro-ethylcarbamoyl)-methyl]-amide (M22.4), 4-[5-(3,5-Dichlorophenyl)-5-trifluoromethyl-4,5-dihydro-isoxazol-3-yl]-N-[(meth-oxyimino)methyl]-2-methylbenzamide (M22.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]tri-azol-1-yl-benzonitrile (M22.8); M.23. Anthranilamide compounds: chloranthraniliprole, cyantra-niliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2HCF_2CF_2CF_2CH_2C(CN)_2CH_2CH_2CF_3$) (M24.1) and 2-(2,2,3,3,4,4,5,5-octafluoropentyl)-2-(3,3,4,4,4-pentafluorobutyl)-malonodinitrile ($CF_2HCF_2CF_2CF_2CH_2C(CN)_2$—$CH_2CH_2CF_2CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl) amino}furan-2(5H)-on (M26.2), 4-{[(2-Chloro1,3-thiazolo-5-yl)methyl](2-fluoroethyl)amino}furan-2(5H)-on (M26.3), 4-{[(6-Chloropyrid-3-yl)methyl](2-fluoroethyl) amino}furan-2(5H)-on (M26.4), 4-{[(6-Chloropyrid-3-yl) methyl] (2,2-difluoroethyl)amino}furan-2(5H)-on (M26.5), 4-{[(6-Chloro-5-fluoropyrid-3-yl)methyl](methyl) amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl) amino}furan-2(5H)-on (M26.8), 4-{[(6-Chloropyrid-3-yl) methyl](cyclopropyl)amino}furan-2(5H)-on (M26.9) and 4-{[(6-Chloropyrid-3-yl)methyl](methyl)amino}furan-2 (5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propan-ecarboxamide-2-(2,6-dichloro-α,α,α-trifluoro-p-tolyl)hydrazone or N—R'-2,2-di (R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a, 12b-decahydro-[2-hydroxy-4,6a,12b-trimethyl-11-oxo-9-(3-pyridinyl)-2H,11H-naphtho[2,1-b]pyrano[3,4-e]pyran-3, 6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822, 779.-AKD 1022 and its preparation have been described in U.S. Pat. No. 6,300,348.-M21.1 is known from WO 2007/101540.-Isoxazolines M22.1 to M22.8 have been described in e.g. WO2005/085216, WO 2007/079162, WO 2007/026965, WO 2009/126668 and WO2009/051956. Anthranilamides M23.1 to M23.6 have been described in WO 2008/72743 and WO 200872783, those M23.7 to M23.12 in WO 2007/043677. Malononitriles M24.1 and M24.2 have been described in WO 02/089579, WO 02/090320, WO 02/090321, WO 04/006677, WO 05/068423, WO 05/068432 and WO 05/063694. M26.1 to M6.10 have been described eg. in WO 2007/115644. M27.1 is described e.g. in JP 2006131529. Organic sulfur compounds have been described in WO 2007060839. M27.2 has been described in WO 2008/66153 and WO 2008/108491. M27.3 has been described in JP 2008/115155.

The following list F of active substances, in conjunction with which the compounds according to the invention can be used, is intended to illustrate the possible combinations but does not limit them:

F.I) Respiration Inhibitors

F.I-1) Inhibitors of complex III at Qo site (e.g. strobilurins)

strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxy-imino-N methyl-acetamide;

oxazolidinediones and imidazolinones: famoxadone, fenamidone;

F.I-2) Inhibitors of complex II (e.g. carboxamides):

carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of complex III at Qi site: cyazofamid, amisulbrom;

F.I-4) Other respiration inhibitors (complex I, uncouplers)

diflumetorim; tecnazen; ferimzone; ametoctradin; silthiofam;

nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine;

F.II-2) Delta14-reductase inhibitors (Amines, e.g. morpholines, piperidines)

morpholines: aldimorph, dodemorph, dodemorph-acetate, fenpropimorph, tridemorph;

piperidines: fenpropidin, piperalin;

spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase) hydroxy (2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)-[1,2,4]triazolo[1,5 a]pyrimidine F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Mmethionine synthesis inhibitors (anilino-pyrimidines)

anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)

dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos;

dithiolanes: isoprothiolane;

F.VII-2) Lipid peroxidation aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandipropamid, pyrimorph;

valinamide carbamates: benthiavalicarb, iprovalicarb, pyribencarb, valifenalate and N-(1-(1-(4-cyano-phenyl) ethanesulfonyl)-but-2-yl)carbamic acid-(4-fluorophenyl)ester;

F.VII-4) Compounds affecting cell membrane permeability and fatty acids carbamates: propamocarb, propamocarb-hydrochlorid F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitrophenyl)-N-ethyl-4-methyl-benzenesulfonamide;

F.VIII-4) Guanidines: guanidine, dodine, dodine free base, guazatine, guazatine-acetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-5-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propyl-chromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethyl-silanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-di-methylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodo-benzoic acid, trinexapac-ethyl and uniconazole;

F.XII) Biological control agents antifungal biocontrol agents: *Bacillus* substilis strain with NRRL No. B-21661 (e.g. RHAPSO-DY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), *Ulocladium oudemansii* (e.g. the product BOTRY-ZEN from BotriZen Ltd., New Zealand), Chitosan (e.g. ARMOUR-ZEN from BotriZen Ltd., New Zealand).

The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, *petunias, geranium/pelargoniums*, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitoes, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxy-methylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-H-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246, WO 92/00377, EP-A 257 993, U.S. Pat. No. 5,013,659) or in transgenic crop plants, for example cotton, with the capability of producing Bacillus thuringiensis toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

In the treatment of seed, the application rates of the compounds of the present invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planters box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "un-sown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previ-ous dilution with water, until the composition is distributed uniformly on the seed. If ap-propriate, this is followed by a drying step.

EXAMPLES

A. Preparation Examples

With appropriate modification of the starting materials, the procedures given in the synthesis examples below were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) determined by HPLC-MS or HPLC spectrometry.

HPLC-MS=high performance liquid chromatography-coupled mass spectrometry; HPLC methods:

Method 1: RP-18 column (Chromolith® Speed ROD from Merck KgaA, Germany), 50*4.6 mm; mobile phase: acetonitrile+0.1% trifluoroacetic acid (TFA)/water+0.1% TFA, using a gradient of 5:95 to 100:0 over 5 minutes at 40° C., flow rate 1.8 ml/min.

Method 2: Phenomenex Kinetex 1.7 µm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 ml/min in 1.50 minutes at 60° C.MS: quadrupole electrospray ionization, 80 V (positive mode).

Method 3: Column: CHIRALPAK® IA 5 µm-250×4.6 mm; mobile phase: heptane/dichloromethane/ethanol/diethylamine 50/50/1/0.1; flow: 1 ml/min; detection: UV 280 nm; 25° C.

Method 4: Column: CHIRALPAK® IC 5 µm-250×4.6 mm; mobile phase: ethanol/methanol 50/50; flow: 0.7 ml/min; detection: UV 280 nm; 25° C.

Example 1

Preparation of 5-methyl-1-(2,2,2-trifluoro-1-trifluoromethyl-ethyl)-1H-pyrazole-4-carboxylic acid pyridazin-4-ylamide [I-34]

A solution of 398 mg 5-methyl-1-[2,2,2-trifluoro-1-(trifluoromethyl)ethyl]pyrazole-4-carbonyl chloride in 10 ml $CH_2Cl_2$ was added dropwise to a solution of 185 mg pyridazin-4-amine and 750 mg triethylamine in 30 ml $CH_2Cl_2$ at 0° C. The mixture was stirred at 20-25° C. for about 68 h, diluted with 25 ml ethylacetate, washed with 3×15 ml sat. aq. $NH_4Cl$ solution, dried over $MgSO_4$ and evaporated. Purification by flash chromatography ($CH_2Cl_2$/MeOH) gave 160 mg of the title compound (90% purity). HPLC-MS (Method 1): RT 2.278 min, m/z $[MH]^+$ 354.1.

Example 2

Preparation of N,5-dimethyl-N-pyridazin-4-yl-1-[2,2,2-trifluoro-1-(trifluoromethyl)ethyl]pyrazole-4-carboxamide [I-38]

A mixture of 300 mg 5-methyl-1-[2,2,2-trifluoro-1-(trifluoromethyl)ethyl]pyrazole-4-carboxylic acid, 127 mg N-methylpyridazin-4-amine, 710 mg O-(7-azabenzotriazol-1-yl)-N,N,N',N'-tetramethyluronium hexafluorophosphate [HATU] and 220 mg triethylamine in 30 ml THF was stirred at 20-25° C. for about 24 h, then evaporated. The residue was taken up in 21 ml $CH_2Cl_2$, washed with 3×14 ml water, dried over $Na_2SO_4$, then evaporated. Purification by flash chromatography ($CH_2Cl_2$/MeOH) gave 130 mg of the title compound (90% purity).

HPLC-MS (Method 1): RT 2.271 min, m/z $[MH]^+$ 368.1.

Example 3

Separation of enantiomers I-381 and I-382 was effected by preparative chromatography under following conditions: Column: CHIRALPAK® AD-H 5 μm-250×30 mm; mobile phase: carbon dioxide/ethanol 90/10; flow: 120 ml/min; detection: UV 280 nm; back pressure: 150 bar; temperature: 25° C.

2 g crude material I-377 yielded in 978 mg (+)-enantiomer I-381, and 972 mg (−)-enantiomer I-382, each >99% ee.

Example 4

Separation of enantiomers I-383 and I-384 was effected by preparative chromatography under following conditions: CHIRALPAK® IC 5 μm-250×30 mm; mobile phase: carbon dioxide/ethanol 70/30; flow: 120 ml/min; detection: UV 280 nm; back pressure: 150 bar; temperature: 25° C.

2 g crude material I-373 yielded in 864 mg (+)-enantiomer I-383 (98.4% ee), and 898 mg (−)-enantiomer I-384 (98.0% ee).

TABLE I

Compounds of formula I (Isomer T-A)

| No. | T | U | $R^1$ | $R^2$ | $R^3$ | $R^4$ | $R^5$ | RT [min] | Method | m/z $[MH]^+$ |
|---|---|---|---|---|---|---|---|---|---|---|
| I-1 | O | N | H | $CH_3$ | —$CH_2CH_2$— | | H | 1.599 | 1 | 244.1 |
| I-2 | O | N | H | $CH_3$ | $CH_2S(O)_2CH_3$ | $CH_3$ | $CH_3$ | 1.553 | 1 | 338.1 |
| I-3 | O | N | $CH_3$ | $CH_3$ | $CH_2S(O)_2CH_3$ | $CH_3$ | $CH_3$ | 1.520 | 1 | 352.1 |
| I-4 | O | N | H | $CH_3$ | $CH_2OCH_3$ | $CH_3$ | H | 1.714 | 1 | 276.1 |
| I-5 | O | N | $CH_3$ | $CH_3$ | $CH_2OCH_3$ | $CH_3$ | H | 1.638 | 1 | 290.2 |
| I-6 | O | N | $CH_2CH_3$ | $CH_3$ | —$(CH_2)_4$— | | H | 2.289 | 1 | 300.2 |
| I-7 | O | N | $CH_3$ | $CH_3$ | —$(CH_2)_4$— | | H | 2.114 | 1 | 286.2 |
| I-8 | O | N | H | $CH_3$ | —$(CH_2)_4$— | | H | 2.169 | 1 | 272.1 |
| I-9 | O | N | H | $CH_3$ | $CH_2CH_3$ | $CH_3$ | H | 2.014 | 1 | 260.1 |
| I-10 | O | N | $CH_2CH_3$ | $CH_3$ | $CH_2CH_3$ | $CH_3$ | H | 2.119 | 1 | 288.2 |
| I-11 | O | N | $CH_3$ | $CH_3$ | $CH_2CH_3$ | $CH_3$ | H | 1.941 | 1 | 274.2 |
| I-12 | O | N | H | $CH_3$ | —$(CH_2)_5$— | | H | 2.383 | 1 | 286.2 |
| I-13 | O | N | $CH_3$ | $CH_3$ | —$(CH_2)_5$— | | H | 2.306 | 1 | 300.2 |
| I-14 | O | N | $CH_2CH_3$ | $CH_3$ | —$(CH_2)_5$— | | H | 2.459 | 1 | 314.2 |
| I-15 | O | N | $CH_2CH_3$ | $CH_3$ | —$(CH_2)_3$— | | H | 2.105 | 1 | 286.2 |
| I-16 | O | N | $CH_3$ | $CH_3$ | —$(CH_2)_3$— | | H | 1.876 | 1 | 272.1 |
| I-17 | O | N | $CH_3$ | $CH_3$ | $CH_2C(CH_3)_2OCH_3$ | $CH_3$ | H | 2.098 | 1 | 332.2 |
| I-18 | O | N | $CH_2CH_3$ | $CH_3$ | $CH_2C(CH_3)_2OCH_3$ | $CH_3$ | H | 2.229 | 1 | 346.2 |
| I-19 | O | N | H | $CH_3$ | —$(CH_2)_3$— | | H | 1.984 | 1 | 258.1 |
| I-20 | O | N | H | $CH_3$ | $CH_2C(CH_3)_2OCH_3$ | $CH_3$ | H | 2.118 | 1 | 318.2 |
| I-21 | O | N | H | $CH_3$ | —$CH_2CH_2OCH_2CH_2$— | | H | 1.643 | 1 | 288.1 |
| I-22 | O | N | $CH_2CH_3$ | $CH_3$ | —$CH_2CH_2OCH_2CH_2$— | | H | 1.634 | 1 | 316.1 |
| I-23 | O | N | $CH_3$ | $CH_3$ | —$CH_2CH_2OCH_2CH_2$— | | H | 1.562 | 1 | 302.2 |
| I-24 | O | N | $CH_2OCH_2CH_3$ | $CH_3$ | c-$C_3H_5$ | $CH_3$ | H | 2.416 | 1 | 330.2 |
| I-25 | O | N | H | $CH_3$ | $CH_2OCH_3$ | $CH_3$ | $CH_3$ | 1.965 | 1 | 290.2 |
| I-26 | O | N | $CH_3$ | $CH_3$ | $CH_2OCH_3$ | $CH_3$ | $CH_3$ | 1.908 | 1 | 304.2 |
| I-27 | O | N | $CH_2OCH_2CH_3$ | $CH_3$ | $CF_3$ | $CH_3$ | H | 2.463 | 1 | 358.1 |
| I-28 | O | N | $CH_3$ | $CH_3$ | $CF_2CHFCF_3$ | $CH_3$ | H | 2.562 | 1 | 396.1 |
| I-29 | O | N | $CH_3$ | $CH_3$ | $CF_2CHF_2$ | $CH_3$ | H | 2.106 | 1 | 346.1 |
| I-30 | O | N | H | $CH_3$ | $CF_2CHFCF_3$ | $CH_3$ | H | 2.552 | 1 | 382.1 |
| I-31 | O | N | H | $CH_3$ | $CF_2CHF_2$ | $CH_3$ | H | 2.144 | 1 | 332.1 |
| I-32 | O | N | H | $CH_3$ | CN | $CH_3$ | $CH_3$ | 1.817 | 1 | 271.1 |
| I-33 | O | N | $CH_3$ | $CH_3$ | CN | $CH_3$ | $CH_3$ | 1.762 | 1 | 285.0 |
| I-34 | O | N | H | $CH_3$ | $CF_3$ | $CF_3$ | H | 2.278 | 1 | 354.1 |
| I-35 | O | N | H | $CH_3$ | CN | $CH_3$ | H | 1.423 | 1 | 257.1 |
| I-36 | O | N | $CH_3$ | $CH_3$ | CN | $CH_3$ | H | 1.401 | 1 | 271.1 |
| I-37 | O | N | $CH_2CH_3$ | $CH_3$ | $CF_3$ | $CF_3$ | H | 2.519 | 1 | 382.1 |
| I-38 | O | N | $CH_3$ | $CH_3$ | $CF_3$ | $CF_3$ | H | 2.271 | 1 | 368.1 |
| I-39 | O | N | H | $CH_3$ | 1-F-c-$C_3H_4$ | $CH_3$ | H | 1.910 | 1 | 290.1 |
| I-40 | O | N | $CH_3$ | $CH_3$ | 1-F-c-$C_3H_4$ | $CH_3$ | H | 1.838 | 1 | 304.1 |
| I-41 | O | N | H | $CH_3$ | $C(CH_3)_3$ | $CH_3$ | H | 2.436 | 1 | 288.2 |
| I-42 | O | N | $CH_3$ | $CH_3$ | $C(CH_3)_3$ | $CH_3$ | H | 2.398 | 1 | 302.2 |
| I-43 | O | N | $CH_2OCH_3$ | $CH_3$ | $C(CH_3)_3$ | $CH_3$ | H | 2.509 | 1 | 332.2 |
| I-44 | O | C | H | $CH_3$ | $C(CH_3)_3$ | $CH_3$ | H | 2.282 | 1 | 287.2 |
| I-45 | O | C | $CH_3$ | $CH_3$ | $C(CH_3)_3$ | $CH_3$ | H | 2.139 | 1 | 301.2 |
| I-46 | O | N | $CH_2CH_3$ | $CH_3$ | $C(CH_3)_3$ | $CH_3$ | H | 2.532 | 1 | 316.2 |
| I-47 | O | N | H | $CH_3$ | $CH_2CH_3$ | $CH_2CH_3$ | H | 2.129 | 1 | 274.2 |
| I-48 | O | N | $CH_3$ | $CH_3$ | $CH_2CH_3$ | $CH_2CH_3$ | H | 2.071 | 1 | 288.2 |
| I-49 | O | N | $CH_2OCH_3$ | $CH_3$ | $CH_2CH_3$ | $CH_2CH_3$ | H | 2.231 | 1 | 318.2 |
| I-50 | O | C | H | $CH_3$ | $CH_2CH_3$ | $CH_2CH_3$ | H | 2.110 | 1 | 273.2 |
| I-51 | O | C | $CH_3$ | $CH_3$ | $CH_2CH_3$ | $CH_2CH_3$ | H | 1.946 | 1 | 287.2 |
| I-52 | O | N | H | $CF_3$ | $CH_2CH_3$ | $CH_2CH_3$ | H | 2.734 | 1 | 328.1 |

TABLE I-continued

Compounds of formula I (Isomer T-A)

| No. | T | U | $R^1$ | $R^2$ | $R^3$ | $R^4$ | $R^5$ | RT [min] | Method | m/z [MH]$^+$ |
|---|---|---|---|---|---|---|---|---|---|---|
| I-53 | O | N | $CH_3$ | $CF_3$ | $CH_2CH_3$ | $CH_2CH_3$ | H | 2.788 | 1 | 342.1 |
| I-54 | O | N | $CH_2OCH_3$ | $CF_3$ | $CH_2CH_3$ | $CH_2CH_3$ | H | 2.955 | 1 | 372.2 |
| I-55 | O | C | H | $CF_3$ | $CH_2CH_3$ | $CH_2CH_3$ | H | 2.523 | 1 | 327.1 |
| I-56 | O | N | H | $CF_3$ | $C(CH_3)_3$ | $CH_3$ | H | 2.936 | 1 | 342.1 |
| I-57 | O | N | $CH_3$ | $CF_3$ | $C(CH_3)_3$ | $CH_3$ | H | 3.049 | 1 | 356.2 |
| I-58 | O | N | $CH_2OCH_3$ | $CF_3$ | $C(CH_3)_3$ | $CH_3$ | H | 3.278 | 1 | 386.2 |
| I-59 | O | C | H | $CF_3$ | $C(CH_3)_3$ | $CH_3$ | H | 2.781 | 1 | 341.2 |
| I-60 | O | C | $CH_2OCH_2CH_3$ | $CH_3$ | $c-C_3H_5$ | $CH_3$ | H | 2.134 | 1 | 329.1 |
| I-61 | S | C | $CH_3$ | $CH_3$ | $CF_3$ | $CH_3$ | H | 2.351 | 1 | 329.0 |
| I-62 | S | C | $CH_2CH_3$ | $CH_3$ | $c-C_3H_5$ | $CH_3$ | H | 2.569 | 1 | 315.2 |
| I-63 | S | C | H | $CH_3$ | $CF_3$ | $CH_3$ | H | 2.246 | 1 | 315.1 |
| I-64 | S | C | $CH_2CH_3$ | $CH_3$ | $CF_3$ | $CH_3$ | H | 2.524 | 1 | 343.0 |
| I-65 | O | N | H | $CH_3$ | —$CCl_2CH_2$— |  | H | 2.143 | 1 | 312.0 |
| I-66 | O | N | $CH_3$ | $CH_3$ | —$CCl_2CH_2$— |  | H | 2.073 | 1 | 326.0 |
| I-67 | O | C | $CH_2OCH_2CH_3$ | $CH_3$ | $CF_3$ | $CH_3$ | H | 0.868 | 2 | 357.2 |
| I-68 | O | N | H | $CH_3$ | $CH=CH_2$ | $CH_3$ | H | 0.716 | 2 | 258.0 |
| I-69 | O | N | $CH_3$ | $CH_3$ | $CH=CH_2$ | $CH_3$ | H | 0.708 | 2 | 272.0 |
| I-70 | O | N | $CH_2CH_3$ | $CH_3$ | $CH=CH_2$ | $CH_3$ | H | 0.761 | 2 | 286.1 |
| I-71 | O | N | $CH_2OCH_3$ | $CH_3$ | $CH=CH_2$ | $CH_3$ | H | 0.776 | 2 | 302.1 |
| I-72 | O | C | $CH_3$ | $CF_3$ | $CH_2CH_3$ | $CH_2CH_3$ | H | 2.597 | 1 | 341.1 |
| I-73 | O | N | $CH_3$ | $CH_3$ | —$CH_2CH_2N(CH_3)CH_2CH_2$— |  | H | 0.727 | 2 | 315.1 |
| I-74 | O | N | H | $CH_3$ | $CH_2CN$ | $CH_3$ | H | 1.525 | 1 | 271.1 |
| I-75 | O | N | $CH_3$ | $CH_3$ | $CH_2CN$ | $CH_3$ | H | 1.466 | 1 | 285.1 |
| I-76 | O | N | $CH_2CH_3$ | $CH_3$ | $CH_2CN$ | $CH_3$ | H | 1.647 | 1 | 299.2 |
| I-77 | O | N | $CH_2OCH_3$ | $CH_3$ | $CH_2CN$ | $CH_3$ | H | 1.669 | 1 | 315.1 |
| I-78 | O | C | $CH_2CH_3$ | $CH_3$ | $CH_2CN$ | $CH_3$ | H | 0.613 | 2 | 298.2 |
| I-79 | O | N | $CH_2CH_3$ | $CH_3$ | $CF_3$ | $CH_3$ | $CH_3$ | 0.866 | 2 | 342.2 |
| I-80 | O | N | H | $CH_3$ | $CF_3$ | $CH_3$ | $CH_3$ | 0.797 | 2 | 314 |
| I-81 | O | C | $CH_3$ | $CH_3$ | $CF_3$ | $CH_3$ | $CH_3$ | 0.767 | 2 | 327.2 |
| I-82 | O | N | H | $CH_3$ | —$(CH_2)_5$— |  | CN | 0.831 | 2 | 311.1 |
| I-83 | O | C | H | $CH_3$ | $CF_3$ | $CH_3$ | $CH_3$ | 0.783 | 2 | 313.2 |
| I-84 | O | C | $CH_3$ | $CH_3$ | —$(CH_2)_5$— |  | CN | 0.809 | 2 | 324.1 |
| I-85 | O | N | $CH_3$ | $CH_3$ | $CF_3$ | $CH_3$ | $CH_3$ | 0.806 | 2 | 328.1 |
| I-86 | O | C | $CH_2CH_3$ | $CH_3$ | $CF_3$ | $CH_3$ | $CH_3$ | 0.833 | 2 | 341.1 |
| I-87 | O | N | $CH_2OCH_2CH_3$ | $CH_3$ | $CF_3$ | $CH_3$ | $CH_3$ | 0.944 | 2 | 372.2 |
| I-88 | O | N | $CH_2OCH_3$ | $CH_3$ | $CF_3$ | $CH_3$ | $CH_3$ | 0.884 | 2 | 358.2 |
| I-89 | O | N | H | $CH_3$ | —$CH_2CH_2N(CH_3)CH_2CH_2$— |  | H | 0.502 | 2 | 301.2 |
| I-90 | O | C | H | $CH_3$ | —$CH_2CH_2N(CH_3)CH_2CH_2$— |  | H | 0.497 | 2 | 300.1 |
| I-91 | O | C | $CH_2OCH_3$ | $CH_3$ | $CF_3$ | $CH_3$ | $CH_3$ | 0.848 | 2 | 357.2 |
| I-92 | O | N | $CH_3$ | $CH_3$ | $1-CN-c-C_3H_4$ | $CH_3$ | H | 1.584 | 1 | 311.1 |
| I-93 | O | N | H | $CH_3$ | $1-CN-c-C_3H_4$ | $CH_3$ | H | 1.739 | 1 | 297.1 |
| I-94 | O | C | H | $CH_3$ | $CH_2CN$ | $CH_3$ | H | 1.504 | 1 | 270.1 |
| I-95 | O | N | H | $CH_3$ | $CH(CH_3)_2$ | $CH_3$ | H | 2.108 | 1 | 274.1 |
| I-96 | O | N | $CH_3$ | $CH_3$ | $CH(CH_3)_2$ | $CH_3$ | H | 2.063 | 1 | 288.1 |
| I-97 | O | N | $CH_2OCH_3$ | $CH_3$ | $CH(CH_3)_2$ | $CH_3$ | H | 0.946 | 2 | 318.1 |
| I-98 | O | N | $CH_2CH_3$ | $CH_3$ | $CH(CH_3)_2$ | $CH_3$ | H | 0.838 | 2 | 302.4 |
| I-99 | O | C | H | $CH_3$ | $CH(CH_3)_2$ | $CH_3$ | H | 2.030 | 1 | 273.1 |
| I-100 | O | C | $CH_3$ | $CH_3$ | $CH(CH_3)_2$ | $CH_3$ | H | 1.859 | 1 | 287.1 |
| I-101 | O | C | $CH_2CH_3$ | $CH_3$ | $CH(CH_3)_2$ | $CH_3$ | H | 2.000 | 1 | 301.1 |
| I-102 | O | N | H | $CH_3$ | $CF_3$ | $CH_2CH_3$ | H | 0.795 | 2 | 314.2 |
| I-103 | O | N | $CH_3$ | $CH_3$ | $CF_3$ | $CH_2CH_3$ | H | 2.011 | 1 | 328.1 |
| I-104 | O | N | $CH_2CH_3$ | $CH_3$ | $CF_3$ | $CH_2CH_3$ | H | 2.172 | 1 | 342.1 |
| I-105 | O | N | $CH_2OCH_3$ | $CH_3$ | $CF_3$ | $CH_2CH_3$ | H | 2.210 | 1 | 358.1 |
| I-106 | O | C | H | $CH_3$ | $CF_3$ | $CH_2CH_3$ | H | 2.128 | 1 | 313.1 |
| I-107 | O | C | $CH_3$ | $CH_3$ | $CF_3$ | $CH_2CH_3$ | H | 1.956 | 1 | 327.1 |
| I-108 | O | C | $CH_2CH_2OCH_3$ | $CH_3$ | $CF_3$ | $CH_2CH_3$ | H | 2.146 | 1 | 357.0 |
| I-109 | O | C | $CH_3$ | $CH_3$ | $CH_2CN$ | $CH_3$ | H | 1.307 | 1 | 284.0 |
| I-110 | O | N | $CH_3$ | $CH_3$ | —$(CH_2)_5$— |  | $CF_3$ | 2.596 | 1 | 368.1 |
| I-111 | O | N | $CH_2CH_3$ | $CH_3$ | —$(CH_2)_5$— |  | $CF_3$ | 2.719 | 1 | 382.1 |
| I-112 | O | N | $CH_2OCH_2CH_3$ | $CH_3$ | —$(CH_2)_5$— |  | $CF_3$ | 1.075 | 2 | 412.2 |
| I-113 | O | N | $CH_2OCH_3$ | $CH_3$ | —$(CH_2)_5$— |  | $CF_3$ | 2.775 | 1 | 398.1 |
| I-114 | O | N | H | $CH_3$ | —$(CH_2)_5$— |  | $CF_3$ | 0.948 | 2 | 354.2 |
| I-115 | O | C | $CH_2OCH_2CH_3$ | $CH_3$ | $CF_3$ | $CH_3$ | $CH_3$ | 0.812 | 2 | 371.4 |
| I-116 | O | C | H | $CH_3$ | $CH_2C_6H_5$ | $CH_3$ | H | 0.842 | 2 | 321.1 |
| I-117 | O | C | $CH_3$ | $CH_3$ | $CH_2C_6H_5$ | $CH_3$ | H | 0.842 | 2 | 335.2 |
| I-118 | O | C | $CH_2CH_3$ | $CH_3$ | $CH_2C_6H_5$ | $CH_3$ | H | 0.899 | 2 | 349.2 |
| I-119 | O | N | H | $CH_3$ | $CH_2C_6H_5$ | $CH_3$ | H | 0.866 | 2 | 322.1 |
| I-120 | O | N | $CH_3$ | $CH_3$ | $CH_2C_6H_5$ | $CH_3$ | H | 0.874 | 2 | 336.2 |
| I-121 | O | N | $CH_2CH_3$ | $CH_3$ | $CH_2C_6H_5$ | $CH_3$ | H | 0.923 | 2 | 350.3 |
| I-122 | O | C | H | $CH_3$ | —$(CH_2)_5$— |  | $CF_3$ | 0.917 | 2 | 353.2 |
| I-123 | O | C | $CH_3$ | $CH_3$ | —$(CH_2)_5$— |  | $CF_3$ | 0.917 | 2 | 367.1 |
| I-124 | O | C | $CH_2CH_3$ | $CH_3$ | —$(CH_2)_5$— |  | $CF_3$ | 0.975 | 2 | 381.1 |
| I-125 | O | N | H | $CH_3$ | 3-<PY> | $CH_3$ | H | 1.198 | 1 | 309.1 |
| I-126 | O | N | H | $CH_3$ | 4-<PY> | $CH_3$ | H | 1.217 | 1 | 309.1 |

TABLE I-continued

Compounds of formula I (Isomer T-A)

| No. | T | U | $R^1$ | $R^2$ | $R^3$ | $R^4$ | $R^5$ | RT [min] | Method | m/z [MH]$^+$ |
|---|---|---|---|---|---|---|---|---|---|---|
| I-127 | O | N | CH$_3$ | CH$_3$ | 4-<PY> | CH$_3$ | H | 1.159 | 1 | 323.1 |
| I-128 | O | N | CH$_2$CH$_3$ | CH$_3$ | —CH$_2$CH$_2$OCH$_2$CH$_2$— | | CF$_3$ | 0.841 | 2 | 384.1 |
| I-129 | O | N | CH$_3$ | CH$_3$ | —CH$_2$CH$_2$OCH$_2$CH$_2$— | | CF$_3$ | 0.791 | 2 | 370.1 |
| I-130 | O | N | H | CH$_3$ | —CH$_2$CH$_2$OCH$_2$CH$_2$— | | CF$_3$ | 0.778 | 2 | 356.1 |
| I-131 | O | C | CH$_3$ | CH$_3$ | —CH$_2$CH$_2$OCH$_2$CH$_2$— | | CF$_3$ | 1.865 | 1 | 369.1 |
| I-132 | O | C | H | CH$_3$ | —CH$_2$CH$_2$OCH$_2$CH$_2$— | | CF$_3$ | 0.761 | 2 | 355.1 |
| I-133 | O | N | H | CH$_3$ | CH$_2$CH$_2$OCH$_3$ | CH$_3$ | H | 1.717 | 1 | 290.1 |
| I-134 | O | N | CH$_3$ | CH$_3$ | CH$_2$CH$_2$OCH$_3$ | CH$_3$ | H | 1.667 | 1 | 304.1 |
| I-135 | O | C | H | CH$_3$ | CH$_2$CH$_2$OCH$_3$ | CH$_3$ | H | 0.666 | 2 | 289.5 |
| I-136 | O | C | CH$_3$ | CH$_3$ | CH$_2$CH$_2$OCH$_3$ | CH$_3$ | H | 1.538 | 1 | 303.1 |
| I-137 | O | C | CH$_2$CH$_3$ | CH$_3$ | CH$_2$CH$_2$OCH$_3$ | CH$_3$ | H | 0.717 | 2 | 317.6 |
| I-138 | O | N | CH$_2$CH$_3$ | CH$_3$ | CH$_2$CH$_2$OCH$_3$ | CH$_3$ | H | 0.747 | 2 | 318.5 |
| I-139 | O | N | CH$_3$ | CH$_3$ | —(CH$_2$)$_5$— | | CN | 2.226 | 1 | 325.1 |
| I-140 | O | C | CH$_2$CH$_3$ | CH$_3$ | —(CH$_2$)$_5$— | | CN | 2.343 | 1 | 338.2 |
| I-141 | O | N | H | CH$_3$ | CH$_2$F | CH$_3$ | H | 0.654 | 2 | 264.0 |
| I-142 | O | N | CH$_3$ | CH$_3$ | CH$_2$F | CH$_3$ | H | 0.645 | 2 | 278.3 |
| I-143 | O | N | CH$_2$CH$_3$ | CH$_3$ | CH$_2$F | CH$_3$ | H | 0.719 | 2 | 292.3 |
| I-144 | O | C | CH$_2$CH$_3$ | CH$_3$ | CH$_2$F | CH$_3$ | H | 0.684 | 2 | 291.2 |
| I-145 | O | C | H | CH$_3$ | CH$_2$F | CH$_3$ | H | 1.443 | 1 | 263.1 |
| I-146 | O | C | CH$_3$ | CH$_3$ | CH$_2$F | CH$_3$ | H | 1.008 | 1 | 277.1 |
| I-147 | O | N | CH$_3$ | CH$_3$ | 3-<PY> | CH$_3$ | H | 1.034 | 1 | 323.1 |
| I-148 | O | N | CH$_2$CH$_3$ | CH$_3$ | 3-<PY> | CH$_3$ | H | 1.300 | 1 | 337.1 |
| I-149 | O | C | CH$_2$CH$_3$ | CH$_3$ | 3-<PY> | CH$_3$ | H | 1.243 | 1 | 336.1 |
| I-150 | O | C | CH$_3$ | CH$_3$ | 3-<PY> | CH$_3$ | H | 1.056 | 1 | 322.1 |
| I-151 | O | C | H | CH$_3$ | 3-<PY> | CH$_3$ | H | 1.124 | 1 | 308.1 |
| I-152 | O | C | H | CH$_3$ | —(CH$_2$)$_5$— | | CN | 2.275 | 1 | 310.1 |
| I-153 | O | N | CH$_2$CH$_3$ | CH$_3$ | —(CH$_2$)$_5$— | | CN | 0.906 | 2 | 339.5 |
| I-154 | O | N | H | CH$_3$ | CHFCH$_3$ | CH$_3$ | H | 0.708 (A) | 2 | 278.2 |
| I-155 | O | N | CH$_3$ | CH$_3$ | CHFCH$_3$ | CH$_3$ | H | 0.708 (A) | 2 | 292.5 |
| I-156 | O | N | CH$_2$CH$_3$ | CH$_3$ | CHFCH$_3$ | CH$_3$ | H | 0.765 (A) | 2 | 306.1 |
| I-157 | O | C | H | CH$_3$ | CHFCH$_3$ | CH$_3$ | H | 0.686 (A) | 2 | 277.3 |
| I-158 | O | C | CH$_3$ | CH$_3$ | CHFCH$_3$ | CH$_3$ | H | 0.677 (A) | 2 | 291.2 |
| I-159 | O | C | CH$_2$CH$_3$ | CH$_3$ | CHFCH$_3$ | CH$_3$ | H | 0.731 (A) | 2 | 305.5 |
| I-160 | O | C | H | CH$_3$ | 4-<PY> | CH$_3$ | H | 0.504 | 2 | 308.1 |
| I-161 | O | N | H | CH$_3$ | CHFCH$_3$ | CH$_3$ | H | 0.698 (B) | 2 | 278.1 |
| I-162 | O | N | CH$_3$ | CH$_3$ | CHFCH$_3$ | CH$_3$ | H | 0.692 (B) | 2 | 292.3 |
| I-163 | O | N | CH$_2$CH$_3$ | CH$_3$ | CHFCH$_3$ | CH$_3$ | H | 0.743 (B) | 2 | 306.1 |
| I-164 | O | C | H | CH$_3$ | CHFCH$_3$ | CH$_3$ | H | 0.675 (B) | 2 | 277.1 |
| I-165 | O | C | CH$_3$ | CH$_3$ | —CH$_2$CH$_2$OCH$_2$CH$_2$— | | CF$_3$ | 0.756 (S) | 2 | 369.1 |
| I-166 | O | C | CH$_2$CH$_3$ | CH$_3$ | —CH$_2$CH$_2$OCH$_2$CH$_2$— | | CF$_3$ | 2.010 (S) | 1 | 383.1 |
| I-167 | O | N | H | CH$_3$ | C$_6$H$_5$ | CH$_3$ | H | 0.837 | 2 | 308.3 |
| I-168 | O | N | CH$_3$ | CH$_3$ | C$_6$H$_5$ | CH$_3$ | H | 0.842 | 2 | 322.3 |
| I-169 | O | N | CH$_2$CH$_3$ | CH$_3$ | C$_6$H$_5$ | CH$_3$ | H | 0.884 | 2 | 336.3 |
| I-170 | O | C | H | CH$_3$ | C$_6$H$_5$ | CH$_3$ | H | 0.792 | 2 | 307.4 |
| I-171 | O | C | CH$_3$ | CH$_3$ | C$_6$H$_5$ | CH$_3$ | H | 0.792 | 2 | 321.1 |
| I-172 | O | C | CH$_2$CH$_3$ | CH$_3$ | C$_6$H$_5$ | CH$_3$ | H | 0.845 | 2 | 335.5 |
| I-173 | O | N | CH$_2$CH$_3$ | CH$_3$ | CN | CH$_3$ | CH$_3$ | 0.747 | 2 | 299.3 |
| I-174 | O | N | CH$_2$CH$_3$ | CH$_3$ | CO$_2$CH$_3$ | CH$_3$ | CH$_3$ | 0.773 | 2 | 332.3 |
| I-175 | O | N | H | CH$_3$ | <TP>-4 | CH$_3$ | H | 0.695 | 2 | 316.4 |
| I-176 | O | N | CH$_3$ | CH$_3$ | <TP>-4 | CH$_3$ | H | 0.690 | 2 | 330.5 |
| I-177 | O | N | CH$_2$CH$_3$ | CH$_3$ | <TP>-4 | CH$_3$ | H | 0.740 | 2 | 344.6 |
| I-178 | O | C | CH$_2$CH$_3$ | CH$_3$ | <TP>-4 | CH$_3$ | H | 0.721 | 2 | 343.3 |
| I-179 | O | C | H | CH$_3$ | <TP>-4 | CH$_3$ | H | 1.682 | 1 | 315.1 |
| I-180 | O | C | CH$_3$ | CH$_3$ | <TP>-4 | CH$_3$ | H | 0.664 | 2 | 329.3 |
| I-181 | O | N | CH$_3$ | CH$_3$ | —CH$_2$CH$_2$— | | CN | 0.625 | 2 | 283.0 |
| I-182 | O | N | H | CH$_3$ | —CH$_2$CH$_2$— | | CN | 0.634 | 2 | 269.1 |
| I-183 | O | N | CH$_2$CH$_3$ | CH$_3$ | —CH$_2$CH$_2$— | | CN | 0.679 | 2 | 297.0 |
| I-184 | O | C | CH$_2$CH$_3$ | CH$_3$ | CHFCH$_3$ | CH$_3$ | H | 0.656 (B) | 2 | 305.4 |
| I-185 | O | C | CH$_3$ | CH$_3$ | CHFCH$_3$ | CH$_3$ | H | 0.656 (B) | 2 | 291.3 |
| I-186 | O | C | CH$_2$CH$_3$ | CH$_3$ | 4-<PY> | CH$_3$ | H | 1.293 | 1 | 336.1 |
| I-187 | O | C | CH$_3$ | CH$_3$ | 4-<PY> | CH$_3$ | H | 1.088 | 1 | 322.1 |
| I-188 | O | N | H | CH$_3$ | 2-<PY> | CH$_3$ | H | 0.611 | 2 | 309.3 |
| I-189 | O | N | CH$_3$ | CH$_3$ | 2-<PY> | CH$_3$ | H | 0.601 | 2 | 323.3 |
| I-190 | O | N | CH$_2$CH$_3$ | CH$_3$ | 2-<PY> | CH$_3$ | H | 0.653 | 2 | 337.3 |
| I-191 | O | C | CH$_2$CH$_3$ | CH$_3$ | 2-<PY> | CH$_3$ | H | 0.633 | 2 | 336.5 |
| I-192 | O | C | CH$_3$ | CH$_3$ | 2-<PY> | CH$_3$ | H | 0.581 | 2 | 322.5 |
| I-193 | O | C | H | CH$_3$ | 2-<PY> | CH$_3$ | H | 0.592 | 2 | 308.3 |
| I-194 | O | N | CH$_3$ | CH$_3$ | (6-Cl-3-<PY>)CH$_2$ | CH$_3$ | H | 0.778 | 2 | 371.1 |
| I-195 | O | N | CH$_2$CH$_3$ | CH$_3$ | (6-Cl-3-<PY>)CH$_2$ | CH$_3$ | H | 0.818 | 2 | 385.1 |
| I-196 | O | C | CH$_2$CH$_3$ | CH$_3$ | CN | CH$_3$ | CH$_3$ | 0.720 | 2 | 298.0 |
| I-197 | O | C | CH$_3$ | CH$_3$ | (6-Cl-3-<PY>)CH$_2$ | CH$_3$ | H | 0.761 | 2 | 370.1 |
| I-198 | O | N | CH$_2$CH$_3$ | CH$_3$ | 1-CN-c-C$_3$H$_4$ | CH$_3$ | H | 0.717 | 2 | 325.1 |
| I-199 | O | N | H | CH$_3$ | CHF$_2$ | CH$_3$ | H | 0.687 | 2 | 282.2 |
| I-200 | O | N | CH$_3$ | CH$_3$ | CHF$_2$ | CH$_3$ | H | 0.680 | 2 | 296.3 |

TABLE I-continued

Compounds of formula I (Isomer T-A)

| No. | T | U | $R^1$ | $R^2$ | $R^3$ | $R^4$ | $R^5$ | RT [min] | Method | m/z [MH]$^+$ |
|---|---|---|---|---|---|---|---|---|---|---|
| I-201 | O | N | CH$_2$CH$_3$ | CH$_3$ | CHF$_2$ | CH$_3$ | H | 0.737 | 2 | 310.4 |
| I-202 | O | C | H | CH$_3$ | CHF$_2$ | CH$_3$ | H | 0.666 | 2 | 281.3 |
| I-203 | O | C | CH$_2$CH$_3$ | CH$_3$ | CHF$_2$ | CH$_3$ | H | 0.706 | 2 | 309.3 |
| I-204 | O | C | CH$_3$ | CH$_3$ | CHF$_2$ | CH$_3$ | H | 0.639 | 2 | 295.3 |
| I-205 | O | N | H | CH$_3$ | —C$_6$H$_4$-2-OCH$_2$CH$_2$— | | H | 0.801 | 2 | 336.2 |
| I-206 | O | N | CH$_3$ | CH$_3$ | —C$_6$H$_4$-2-OCH$_2$CH$_2$— | | H | 0.800 | 2 | 350.2 |
| I-207 | O | N | CH$_2$CH$_3$ | CH$_3$ | —C$_6$H$_4$-2-OCH$_2$CH$_2$— | | H | 0.845 | 2 | 364.4 |
| I-208 | O | C | H | CH$_3$ | —C$_6$H$_4$-2-OCH$_2$CH$_2$— | | H | 0.787 | 2 | 335.3 |
| I-209 | O | C | CH$_3$ | CH$_3$ | —C$_6$H$_4$-2-OCH$_2$CH$_2$— | | H | 0.782 | 2 | 349.3 |
| I-210 | O | C | CH$_2$CH$_3$ | CH$_3$ | —C$_6$H$_4$-2-OCH$_2$CH$_2$— | | H | 0.838 | 2 | 363.3 |
| I-211 | O | C | CH$_3$ | CH$_3$ | —CH$_2$S(O)$_2$CH$_2$— | | H | 0.488 | 2 | 321.2 |
| I-212 | O | C | CH$_2$CH$_3$ | CH$_3$ | —CH$_2$S(O)$_2$CH$_2$— | | H | 0.545 | 2 | 335.2 |
| I-213 | O | N | CH$_3$ | CH$_3$ | —CH$_2$CH$_2$N[C(O)CH$_3$]CH$_2$CH$_2$— | | H | 0.605 | 2 | 343.2 |
| I-214 | O | N | CH$_2$CH$_3$ | CH$_3$ | —CH$_2$S(O)$_2$CH$_2$— | | H | 0.603 | 2 | 336.2 |
| I-215 | O | C | H | CH$_3$ | —CH$_2$S(O)$_2$CH$_2$— | | H | 0.511 | 2 | 307.2 |
| I-216 | O | N | H | CH$_3$ | —CH$_2$S(O)$_2$CH$_2$— | | H | 0.523 | 2 | 308.2 |
| I-217 | O | N | CH$_3$ | CH$_3$ | —CH$_2$S(O)$_2$CH$_2$— | | H | 0.511 | 2 | 322.2 |
| I-218 | O | N | CH$_3$ | CH$_3$ | —CH$_2$SCH$_2$— | | H | 0.686 | 2 | 290.1 |
| I-219 | O | N | H | CH$_3$ | —CH$_2$SCH$_2$— | | H | 0.693 | 2 | 276.1 |
| I-220 | O | N | H | CH$_3$ | (6-Cl-3-<PY>)CH$_2$ | CH$_3$ | H | 1.961 | 1 | 357.1 |
| I-221 | O | C | H | CH$_3$ | —CH$_2$SCH$_2$— | | H | 0.677 | 2 | 275.1 |
| I-222 | O | C | CH$_2$CH$_3$ | CH$_3$ | (6-Cl-3-<PY>)CH$_2$ | CH$_3$ | H | 1.986 (S) | 1 | 384.2 |
| I-223 | O | C | CH$_3$ | CH$_3$ | —CH$_2$SCH$_2$— | | H | 0.666 | 2 | 289.1 |
| I-224 | O | C | CH$_2$CH$_3$ | CH$_3$ | —CH$_2$SCH$_2$— | | H | 0.676 | 2 | 303.1 |
| I-225 | O | N | CH$_3$ | CH$_3$ | CH(CH$_3$)$_2$ | CH(CH$_3$)$_2$ | H | 0.914 | 2 | 316.4 |
| I-226 | O | N | H | CH$_3$ | CH(CH$_3$)$_2$ | CH(CH$_3$)$_2$ | H | 0.909 | 2 | 302.3 |
| I-227 | O | C | H | CH$_3$ | CH(CH$_3$)$_2$ | CH(CH$_3$)$_2$ | H | 0.873 | 2 | 301.5 |
| I-228 | O | C | CH$_3$ | CH$_3$ | CH(CH$_3$)$_2$ | CH(CH$_3$)$_2$ | H | 0.881 | 2 | 315.5 |
| I-229 | O | C | CH$_2$CH$_3$ | CH$_3$ | CH(CH$_3$)$_2$ | CH(CH$_3$)$_2$ | H | 0.953 | 2 | 329.4 |
| I-230 | O | C | H | CH$_3$ | CH$_2$CO$_2$CH$_2$CH$_3$ | CH$_3$ | H | 0.716 | 2 | 317.2 |
| I-231 | O | N | H | CH$_3$ | CH$_2$CO$_2$CH$_2$CH$_3$ | CH$_3$ | H | 0.731 | 2 | 318.1 |
| I-232 | O | N | CH$_2$CH$_3$ | CH$_3$ | CH$_2$CO$_2$CH$_2$CH$_3$ | CH$_3$ | H | 0.785 | 2 | 346.2 |
| I-233 | O | N | CH$_3$ | CH$_3$ | CH$_2$CO$_2$CH$_2$CH$_3$ | CH$_3$ | H | 0.736 | 2 | 332.2 |
| I-234 | O | N | CH$_2$CH$_3$ | CH$_3$ | CH(CH$_3$)$_2$ | CH(CH$_3$)$_2$ | H | 0.962 | 2 | 330.5 |
| I-235 | O | N | CH$_2$CH$_3$ | CH$_3$ | —CH$_2$SCH$_2$— | | H | 0.741 | 2 | 304.1 |
| I-236 | O | N | H | CH$_3$ | 2-CH$_3$-1,3-<OTL>-2 | CH$_3$ | H | 0.780 | 2 | 334.3 |
| I-237 | O | N | CH$_3$ | CH$_3$ | 2-CH$_3$-1,3-<OTL>-2 | CH$_3$ | H | 0.784 | 2 | 348.4 |
| I-238 | O | N | CH$_2$CH$_3$ | CH$_3$ | 2-CH$_3$-1,3-<OTL>-2 | CH$_3$ | H | 0.827 | 2 | 362.5 |
| I-239 | O | C | H | CH$_3$ | 2-CH$_3$-1,3-<OTL>-2 | CH$_3$ | H | 0.762 | 2 | 333.3 |
| I-240 | O | C | CH$_3$ | CH$_3$ | 2-CH$_3$-1,3-<OTL>-2 | CH$_3$ | H | 0.750 | 2 | 347.3 |
| I-241 | O | C | CH$_2$CH$_3$ | CH$_3$ | 2-CH$_3$-1,3-<OTL>-2 | CH$_3$ | H | 0.779 | 2 | 361.3 |
| I-242 | O | N | H | CH$_3$ | —CH$_2$S(O)CH$_2$— | | H | 0.507 | 2 | 292.2 |
| I-243 | O | N | CH$_3$ | CH$_3$ | —CH$_2$S(O)CH$_2$— | | H | 0.487 | 2 | 306.2 |
| I-244 | O | C | CH$_3$ | CH$_3$ | CN | CH$_3$ | CH$_3$ | 0.668 | 2 | 284.0 |
| I-245 | O | C | H | CH$_3$ | CN | CH$_3$ | CH$_3$ | 0.663 | 2 | 270.3 |
| I-246 | O | N | CH$_3$ | CH$_3$ | CH(CH$_3$)CO$_2$CH$_2$CH$_3$ | CH$_3$ | H | 0.790 | 2 | 346.2 |
| I-247 | O | N | CH$_2$CH$_3$ | CH$_3$ | CH(CH$_3$)CO$_2$CH$_2$CH$_3$ | CH$_3$ | H | 0.834 | 2 | 360.2 |
| I-248 | O | N | H | CH$_3$ | CH(CH$_3$)CO$_2$CH$_2$CH$_3$ | CH$_3$ | H | 0.777 | 2 | 332.1 |
| I-249 | O | N | H | CH$_3$ | <TP>-2-CH$_2$ | CH$_3$ | H | 0.815 | 2 | 330.4 |
| I-250 | O | N | CH$_3$ | CH$_3$ | <TP>-2-CH$_2$ | CH$_3$ | H | 0.823 | 2 | 344.4 |
| I-251 | O | N | CH$_2$CH$_3$ | CH$_3$ | <TP>-2-CH$_2$ | CH$_3$ | H | 0.870 | 2 | 358.5 |
| I-252 | O | C | CH$_2$CH$_3$ | CH$_3$ | <TP>-2-CH$_2$ | CH$_3$ | H | 0.849 | 2 | 357.4 |
| I-253 | O | C | H | CH$_3$ | <TP>-2-CH$_2$ | CH$_3$ | H | 0.801 | 2 | 329.4 |
| I-254 | O | C | CH$_3$ | CH$_3$ | <TP>-2-CH$_2$ | CH$_3$ | H | 0.788 | 2 | 343.4 |
| I-255 | O | N | CH$_2$CH$_3$ | CH$_3$ | —CH$_2$S(O)CH$_2$— | | H | 0.573 | 2 | 320.2 |
| I-256 | O | C | H | CH$_3$ | —CH$_2$S(O)CH$_2$— | | H | 0.488 | 2 | 291.2 |
| I-257 | O | N | H | CH$_3$ | C(O)NHCH$_3$ | CH$_3$ | H | 0.535 | 2 | 289.0 |
| I-258 | O | N | H | CH$_3$ | CH(CH$_2$CH$_3$)CH(CH$_3$)$_2$ | CH$_3$ | H | 0.987 | 2 | 316.5 |
| I-259 | O | N | CH$_3$ | CH$_3$ | CH(CH$_2$CH$_3$)CH(CH$_3$)$_2$ | CH$_3$ | H | 0.987 | 2 | 330.4 |
| I-260 | O | N | CH$_2$CH$_3$ | CH$_3$ | CH(CH$_2$CH$_3$)CH(CH$_3$)$_2$ | CH$_3$ | H | 1.035 | 2 | 344.6 |
| I-261 | O | C | H | CH$_3$ | CH(CH$_2$CH$_3$)CH(CH$_3$)$_2$ | CH$_3$ | H | 0.946 | 2 | 315.4 |
| I-262 | O | C | CH$_3$ | CH$_3$ | CH(CH$_2$CH$_3$)CH(CH$_3$)$_2$ | CH$_3$ | H | 0.959 | 2 | 329.5 |
| I-263 | O | C | CH$_2$CH$_3$ | CH$_3$ | CH(CH$_2$CH$_3$)CH(CH$_3$)$_2$ | CH$_3$ | H | 1.024 | 2 | 343.6 |
| I-264 | O | N | H | CH$_3$ | CH$_2$CH(CH$_3$)$_2$ | CH$_3$ | H | 0.875 | 2 | 288.3 |
| I-265 | O | N | CH$_3$ | CH$_3$ | CH$_2$CH(CH$_3$)$_2$ | CH$_3$ | H | 0.868 | 2 | 302.3 |
| I-266 | O | N | CH$_2$CH$_3$ | CH$_3$ | CH$_2$CH(CH$_3$)$_2$ | CH$_3$ | H | 0.915 | 2 | 316.2 |
| I-267 | O | C | H | CH$_3$ | CH$_2$CH(CH$_3$)$_2$ | CH$_3$ | H | 0.841 | 2 | 287.4 |
| I-268 | O | C | CH$_3$ | CH$_3$ | CH$_2$CH(CH$_3$)$_2$ | CH$_3$ | H | 0.835 | 2 | 301.4 |
| I-269 | O | C | CH$_2$CH$_3$ | CH$_3$ | CH$_2$CH(CH$_3$)$_2$ | CH$_3$ | H | 0.899 | 2 | 315.5 |
| I-270 | O | N | CH$_3$ | CH$_3$ | CO$_2$CH$_2$CH$_3$ | CH$_3$ | H | 0.706 | 2 | 318.1 |
| I-271 | O | N | CH$_2$CH$_3$ | CH$_3$ | CO$_2$CH$_2$CH$_3$ | CH$_3$ | H | 0.758 | 2 | 332.2 |
| I-272 | O | C | CH$_3$ | CH$_3$ | CH$_2$CO$_2$CH$_2$CH$_3$ | CH$_3$ | H | 0.707 | 2 | 331.2 |
| I-273 | O | C | CH$_3$ | CH$_3$ | CO$_2$CH$_2$CH$_3$ | CH$_3$ | H | 0.680 | 2 | 317.2 |
| I-274 | O | N | H | CH$_3$ | CO$_2$CH$_2$CH$_3$ | CH$_3$ | H | 0.708 | 2 | 304.1 |

TABLE I-continued

Compounds of formula I (Isomer T-A)

| No. | T | U | R¹ | R² | R³ | R⁴ | R⁵ | RT [min] | Method | m/z [MH]⁺ |
|---|---|---|---|---|---|---|---|---|---|---|
| I-275 | O | C | H | $CH_3$ | $CO_2CH_2CH_3$ | $CH_3$ | H | 0.693 | 2 | 303.1 |
| I-276 | O | N | H | $CH_3$ | $CF_3$ | $CH(CH_3)_2$ | H | 0.850 | 2 | 328.1 |
| I-277 | O | N | $CH_3$ | $CH_3$ | $CF_3$ | $CH(CH_3)_2$ | H | 0.859 | 2 | 342.0 |
| I-278 | O | N | $CH_2CH_3$ | $CH_3$ | $CF_3$ | $CH(CH_3)_2$ | H | 0.917 | 2 | 356.1 |
| I-279 | O | C | H | $CH_3$ | $CF_3$ | $CH(CH_3)_2$ | H | 0.834 | 2 | 327.3 |
| I-280 | O | C | $CH_3$ | $CH_3$ | $CF_3$ | $CH(CH_3)_2$ | H | 0.842 | 2 | 341.2 |
| I-281 | O | C | $CH_2CH_3$ | $CH_3$ | $CF_3$ | $CH(CH_3)_2$ | H | 0.903 | 2 | 355.3 |
| I-282 | O | N | H | $CH_3$ | 3-<TN> | $CH_3$ | H | 0.740 | 2 | 314.4 |
| I-283 | O | N | $CH_3$ | $CH_3$ | 3-<TN> | $CH_3$ | H | 0.791 | 2 | 328.1 |
| I-284 | O | N | $CH_2CH_3$ | $CH_3$ | 3-<TN> | $CH_3$ | H | 0.847 | 2 | 342.1 |
| I-285 | O | C | H | $CH_3$ | 3-<TN> | $CH_3$ | H | 0.783 | 2 | 313.4 |
| I-286 | O | C | $CH_3$ | $CH_3$ | 3-<TN> | $CH_3$ | H | 0.768 | 2 | 327.3 |
| I-287 | O | C | $CH_2CH_3$ | $CH_3$ | 3-<TN> | $CH_3$ | H | 0.830 | 2 | 341.3 |
| I-288 | O | N | $CH_3$ | $CH_3$ | $C(O)NHCH_3$ | $CH_3$ | H | 0.529 | 2 | 303.3 |
| I-289 | O | C | H | $CH_3$ | —$CH_2CH_2N[C(O)CH_3]CH_2CH_2$— | | H | 0.610 | 2 | 328.3 |
| I-290 | O | N | $CH_2CH_3$ | $CH_3$ | $CF_3$ | c-$C_3H_5$ | H | 0.838 | 2 | 353.4 |
| I-291 | O | N | $CH_3$ | $CH_3$ | $CH_2OC_6H_5$ | $CH_3$ | H | 0.893 | 2 | 352.4 |
| I-292 | O | N | H | $CH_3$ | $CH_2OC_6H_5$ | $CH_3$ | H | 0.885 | 2 | 338.3 |
| I-293 | O | N | $CH_2CH_3$ | $CH_3$ | $CH_2OC_6H_5$ | $CH_3$ | H | 0.931 | 2 | 366.6 |
| I-294 | O | C | $CH_3$ | $CH_3$ | $CH_2OC_6H_5$ | $CH_3$ | H | 0.863 | 2 | 351.3 |
| I-295 | O | C | $CH_2CH_3$ | $CH_3$ | $CH_2OC_6H_5$ | $CH_3$ | H | 0.912 | 2 | 365.4 |
| I-296 | O | C | H | $CH_3$ | $CH_2OC_6H_5$ | $CH_3$ | H | 0.859 | 2 | 337.4 |
| I-297 | O | N | H | $CH_3$ | $CF_3$ | c-$C_3H_5$ | H | 0.826 | 2 | 326.2 |
| I-298 | O | N | $CH_3$ | $CH_3$ | $CF_3$ | c-$C_3H_5$ | H | 0.827 | 2 | 340.3 |
| I-299 | O | N | $CH_2CH_3$ | $CH_3$ | $CF_3$ | c-$C_3H_5$ | H | 0.873 | 2 | 354.3 |
| I-300 | O | C | H | $CH_3$ | $CF_3$ | c-$C_3H_5$ | H | 0.796 | 2 | 325.2 |
| I-301 | O | C | $CH_3$ | $CH_3$ | $CF_3$ | c-$C_3H_5$ | H | 0.781 | 2 | 339.0 |
| I-302 | O | C | H | $CH_3$ | $C(O)NHCH_3$ | $CH_3$ | H | 1.197 | 1 | 288.1 |
| I-303 | O | N | $CH_2CH_3$ | $CH_3$ | $C(O)NHCH_3$ | $CH_3$ | H | 0.601 | 2 | 317.1 |
| I-304 | O | N | H | $CH_3$ | 1-$S(O)_2CH_3$-c-$C_3H_4$ | $CH_3$ | H | 0.661 | 2 | 350.1 |
| I-305 | O | N | $CH_3$ | $CH_3$ | 1-$S(O)_2CH_3$-c-$C_3H_4$ | $CH_3$ | H | 0.665 | 2 | 364.1 |
| I-306 | O | N | $CH_2CH_3$ | $CH_3$ | 1-$S(O)_2CH_3$-c-$C_3H_4$ | $CH_3$ | H | 0.719 | 2 | 378.1 |
| I-307 | O | C | H | $CH_3$ | 1-$S(O)_2CH_3$-c-$C_3H_4$I | $CH_3$ | H | 0.653 | 2 | 349.1 |
| I-308 | O | C | $CH_3$ | $CH_3$ | 1-$S(O)_2CH_3$-c-$C_3H_4$I | $CH_3$ | H | 0.651 | 2 | 363.0 |
| I-309 | O | C | $CH_2CH_3$ | $CH_3$ | 1-$S(O)_2CH_3$-c-$C_3H_4$ | $CH_3$ | H | 0.706 | 2 | 377.2 |
| I-310 | O | C | $CH_3$ | $CF_3$ | $C(CH_3)_3$ | $CH_3$ | H | 2.877 | 1 | 355.1 |
| I-311 | O | C | $CH_2CH_3$ | $CH_3$ | $CO_2CH_2CH_3$ | $CH_3$ | H | 0.730 | 2 | 331.2 |
| I-312 | O | C | $CH_2CH_3$ | $CH_3$ | $CH_2CO_2CH_2CH_3$ | $CH_3$ | H | 0.764 | 2 | 345.2 |
| I-313 | O | N | H | $CH_3$ | 1,1-<DOT>-3 | $CH_3$ | H | 0.603 | 2 | 336.0 |
| I-314 | O | N | $CH_3$ | $CH_3$ | 1,1-<DOT>-3 | $CH_3$ | H | 0.574 | 2 | 350.0 |
| I-315 | O | N | $CH_2CH_3$ | $CH_3$ | 1,1-<DOT>-3 | $CH_3$ | H | 0.666 | 2 | 364.0 |
| I-316 | O | C | H | $CH_3$ | 1,1-<DOT>-3 | $CH_3$ | H | 0.584 | 2 | 335.0 |
| I-317 | O | C | $CH_3$ | $CH_3$ | 1,1-<DOT>-3 | $CH_3$ | H | 0.544 | 2 | 349.0 |
| I-318 | O | N | H | $CH_3$ | 1-$CH_3$-c-$C_3H_4$ | $CH_3$ | H | 0.816 | 2 | 286.2 |
| I-319 | O | N | $CH_2CH_3$ | $CH_3$ | 1-$CH_3$-c-$C_3H_4$ | $CH_3$ | H | 0.870 | 2 | 314.2 |
| I-320 | O | C | H | $CH_3$ | 1-$CH_3$-c-$C_3H_4$ | $CH_3$ | H | 0.790 | 2 | 285.2 |
| I-321 | O | C | $CH_3$ | $CH_3$ | 1-$CH_3$-c-$C_3H_4$ | $CH_3$ | H | 0.768 | 2 | 299.2 |
| I-322 | O | N | $CH_3$ | $CH_3$ | 2,2-$Cl_2$-c-$C_3H_3$ | $CH_3$ | H | 0.827 | 2 | 354.1 |
| I-323 | O | N | H | $CH_3$ | 1,3-<DT>-2-$CH_2$ | $CH_3$ | H | 0.840 | 2 | 364.3 |
| I-324 | O | N | $CH_3$ | $CH_3$ | 1,3-<DT>-2-$CH_2$ | $CH_3$ | H | 0.837 | 2 | 378.4 |
| I-325 | O | N | $CH_2CH_3$ | $CH_3$ | 1,3-<DT>-2-$CH_2$ | $CH_3$ | H | 0.889 | 2 | 392.3 |
| I-326 | O | C | H | $CH_3$ | 1,3-<DT>-2-$CH_2$ | $CH_3$ | H | 0.817 | 2 | 363.3 |
| I-327 | O | C | $CH_3$ | $CH_3$ | 1,3-<DT>-2-$CH_2$ | $CH_3$ | H | 0.812 | 2 | 377.4 |
| I-328 | O | C | $CH_2CH_3$ | $CH_3$ | 1,3-<DT>-2-$CH_2$ | $CH_3$ | H | 0.873 | 2 | 391.4 |
| I-329 | O | N | H | $CH_3$ | $CH_2OH$ | $CH_3$ | H | 0.522 | 2 | 262.0 |
| I-330 | O | N | H | $CH_3$ | —$CH_2CH_2N[C(O)CH_3]CH_2CH_2$— | | H | 0.624 | 2 | 329.1 |
| I-331 | O | N | H | $CH_3$ | $C(CH_3)_2CO_2CH_2CH_3$ | $CH_3$ | H | 0.849 | 2 | 346.1 |
| I-332 | O | N | $CH_3$ | $CH_3$ | $C(CH_3)_2CO_2CH_2CH_3$ | $CH_3$ | H | 0.854 | 2 | 360.5 |
| I-333 | O | N | $CH_2CH_3$ | $CH_3$ | $C(CH_3)_2CO_2CH_2CH_3$ | $CH_3$ | H | 0.908 | 2 | 374.4 |
| I-334 | O | N | H | $CH_3$ | $C(CH_3)_2CN$ | $CH_3$ | H | 0.695 | 2 | 299.0 |
| I-335 | O | N | H | $CH_3$ | <TT>-3 | $CH_3$ | H | 0.745 | 2 | 304.0 |
| I-336 | O | N | $CH_3$ | $CH_3$ | $C(CH_3)_2CN$ | $CH_3$ | H | 0.698 | 2 | 313.1 |
| I-337 | O | N | $CH_3$ | $CH_3$ | <TT>-3 | $CH_3$ | H | 0.751 | 2 | 318.0 |
| I-338 | O | C | $CH_3$ | $CH_3$ | <TT>-3 | $CH_3$ | H | 0.724 | 2 | 317.0 |
| I-339 | O | N | $CH_2CH_3$ | $CH_3$ | $C(CH_3)_2CN$ | $CH_3$ | H | 0.754 | 2 | 327.2 |
| I-340 | O | N | $CH_2CH_3$ | $CH_3$ | 1-<OTT>-3 | $CH_3$ | H | 0.635 | 2 | 348.0 |
| I-341 | O | N | H | $CH_3$ | <TZ>-2 | $CH_3$ | H | 0.680 | 2 | 315.0 |
| I-342 | O | N | $CH_3$ | $CH_3$ | <TZ>-2 | $CH_3$ | H | 0.678 | 2 | 329.0 |
| I-343 | O | N | $CH_2CH_3$ | $CH_3$ | <TZ>-2 | $CH_3$ | H | 0.726 | 2 | 343.1 |
| I-344 | O | N | $CH_2CH_3$ | $CH_3$ | $CH_2CF_3$ | $CH_3$ | H | 0.808 | 2 | 342.1 |
| I-345 | O | N | H | $CH_3$ | $CH_2CF_3$ | $CH_3$ | H | 0.760 | 2 | 314.1 |
| I-346 | O | N | $CH_3$ | $CH_3$ | 1-$CH_3$-c-$C_3H_4$ | $CH_3$ | H | 0.817 | 2 | 300.2 |
| I-347 | O | C | $CH_3$ | $CH_3$ | 2,2-$Cl_2$-c-$C_3H_3$ | $CH_3$ | H | 0.795 (S) | 2 | 353.1 |
| I-348 | O | N | $CH_2CH_3$ | $CH_3$ | 2,2-$Cl_2$-c-$C_3H_3$ | $CH_3$ | H | 0.883 (S) | 2 | 368.1 |

TABLE I-continued

Compounds of formula I (Isomer T-A)

| No. | T | U | R$^1$ | R$^2$ | R$^3$ | R$^4$ | R$^5$ | RT [min] | Method | m/z [MH]$^+$ |
|---|---|---|---|---|---|---|---|---|---|---|
| I-349 | O | C | CH$_2$CH$_3$ | CH$_3$ | 2,2-Cl$_2$-c-C$_3$H$_3$ | CH$_3$ | H | 0.848 (S) | 2 | 367.1 |
| I-350 | O | N | H | CH$_3$ | 2,2-Cl$_2$-c-C$_3$H$_3$ | CH$_3$ | H | 0.831 | 2 | 340.1 |
| I-351 | O | N | CH$_3$ | CH$_3$ | CH$_2$CF$_3$ | CH$_3$ | H | 0.752 | 2 | 328.1 |
| I-352 | O | N | H | CH$_3$ | 1-SCH$_3$-c-C$_3$H$_4$ | CH$_3$ | H | 0.820 | 2 | 318.0 |
| I-353 | O | N | CH$_3$ | CH$_3$ | 1-SCH$_3$-c-C$_3$H$_4$ | CH$_3$ | H | 0.816 | 2 | 332.0 |
| I-354 | O | N | CH$_2$CH$_3$ | CH$_3$ | 1-SCH$_3$-c-C$_3$H$_4$ | CH$_3$ | H | 0.873 | 2 | 346.0 |
| I-355 | O | C | H | CH$_3$ | 1-SCH$_3$-c-C$_3$H$_4$ | CH$_3$ | H | 0.785 | 2 | 317.0 |
| I-356 | O | C | CH$_3$ | CH$_3$ | 1-SCH$_3$-c-C$_3$H$_4$ | CH$_3$ | H | 0.793 | 2 | 331.0 |
| I-357 | O | C | CH$_2$CH$_3$ | CH$_3$ | 1-SCH$_3$-c-C$_3$H$_4$ | CH$_3$ | H | 0.849 | 2 | 345.2 |
| I-358 | O | C | H | CH$_3$ | 2,2-Cl$_2$-c-C$_3$H$_3$ | CH$_3$ | H | 0.801 | 2 | 339.1 |
| I-359 | O | C | CH$_2$CH$_3$ | CH$_3$ | 1-CH$_3$-c-C$_3$H$_4$ | CH$_3$ | H | 0.828 (S) | 2 | 313.2 |
| I-360 | O | N | CH$_2$CH$_3$ | CH$_3$ | CF$_3$ | C(CH$_3$)$_3$ | H | 0.986 | 2 | 370.3 |
| I-361 | O | N | CH$_3$ | CH$_3$ | CF$_3$ | C(CH$_3$)$_3$ | H | 0.926 | 2 | 356.5 |
| I-362 | O | N | H | CH$_3$ | CF$_3$ | C(CH$_3$)$_3$ | H | 0.909 | 2 | 342.4 |
| I-363 | O | N | H | CH$_3$ | 1-CF$_3$-c-C$_3$H$_4$ | CH$_3$ | H | 2.417 | 1 | 340.1 |
| I-364 | O | N | CH$_2$CH$_3$ | CH$_3$ | 1-CF$_3$-c-C$_3$H$_4$ | CH$_3$ | H | 2.535 | 1 | 368.2 |
| I-365 | O | N | CH$_3$ | CH$_3$ | 1-CF$_3$-c-C$_3$H$_4$ | CH$_3$ | H | 0.865 | 2 | 354.1 |
| I-366 | O | N | H | CH$_3$ | c-C$_3$H$_5$ | CH$_3$ | H | 2.047 | 1 | 272.1 |
| I-367 | O | N | CH$_3$ | CH$_3$ | c-C$_3$H$_5$ | CH$_3$ | H | 2.028 | 1 | 286.2 |
| I-368 | O | N | CH$_3$ | CH$_3$ | CF$_3$ | CH$_3$ | H | 0.728 | 2 | 314.1 |
| I-369 | O | N | H | CH$_3$ | CF$_3$ | CH$_3$ | H | 2.025 | 1 | 300.1 |
| I-370 | O | N | CH$_2$CH$_3$ | CH$_3$ | CF$_3$ | CH$_3$ | H | 0.798 | 2 | 328.1 |
| I-371 | O | N | CH$_2$OCH$_3$ | CH$_3$ | c-C$_3$H$_5$ | CH$_3$ | H | 2.133 | 1 | 316.2 |
| I-372 | O | N | CH$_2$OCH$_3$ | CH$_3$ | CF$_3$ | CH$_3$ | H | 2.483 | 1 | 344.1 |
| I-373 | O | C | CH$_3$ | CH$_3$ | c-C$_3$H$_5$ | CH$_3$ | H | 1.801 | 1 | 285.1 |
| I-374 | O | C | H | CH$_3$ | c-C$_3$H$_5$ | CH$_3$ | H | 1.965 | 1 | 271.1 |
| I-375 | O | C | CH$_2$OCH$_3$ | CH$_3$ | c-C$_3$H$_5$ | CH$_3$ | H | 1.954 | 1 | 315.1 |
| I-376 | O | C | H | CH$_3$ | CF$_3$ | CH$_3$ | H | 1.889 | 1 | 299.0 |
| I-377 | O | C | CH$_3$ | CH$_3$ | CF$_3$ | CH$_3$ | H | 1.768 | 1 | 313.1 |
| I-378 | O | C | CH$_2$CH$_3$ | CH$_3$ | c-C$_3$H$_5$ | CH$_3$ | H | 1.976 | 1 | 299.2 |
| I-379 | O | C | CH$_2$CH$_3$ | CH$_3$ | CF$_3$ | CH$_3$ | H | 1.927 | 1 | 327.1 |
| I-380 | O | C | CH$_2$OCH$_3$ | CH$_3$ | CF$_3$ | CH$_3$ | H | 0.776 | 2 | 343.0 |
| I-381 | O | N | CH$_3$ | CH$_3$ | CF$_3$ | CH$_3$ | H | 9.0 (E+) | 3 | |
| I-382 | O | N | CH$_3$ | CH$_3$ | CF$_3$ | CH$_3$ | H | 10.7 (E−) | 3 | |
| I-383 | O | N | CH$_3$ | CH$_3$ | c-C$_3$H$_5$ | CH$_3$ | H | 12.1 (E−) | 4 | |
| I-384 | O | N | CH$_3$ | CH$_3$ | c-C$_3$H$_5$ | CH$_3$ | H | 13.5 (E+) | 4 | |

Abbreviations:
<DOT>: dioxothietanyl
<DT>: dithianyl
<OTL>: oxathiolanyl
<OTT>: oxothietanyl
<PY>: pyridyl
<TN>: thienyl
<TP>: tetrahydropyranyl
<TT>: thietanyl
<TZ>: thiazolyl
(A), (B): diastereomer A, and B, resp.
(S): salt of trifluoroacetic acid
(E+): (+)-enantiomer
(E−): (−)-enantiomer B. Biological Examples The activity of the compounds of formula I of the present invention could be demonstrated and evaluated in biological tests described in the following.

If not otherwise specified the test solutions were prepared as follows:

The active compound was dissolved at the desired concentration in a mixture of 1:1 (vol:vol) distilled water:aceton. The test solution was prepared at the day of use and in general at concentrations of ppm (wt/vol).

B.1 Cowpea Aphid (*Aphis craccivora*)

Potted cowpea plants colonized with 100-150 aphids of various stages were sprayed after the pest population had been recorded. Population reduction was assessed after 24, 72, and 120 hours.

In this test, the compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-50, I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-74, I-75, I-76, I-77, I-78, I-79, I-80, I-81, I-82, I-83, I-84, I-85, I-86, I-87, I-88, I-91, I-92, I-93, I-94, I-95, I-96, I-97, I-98, I-99, I-100, I-101, I-102, I-103, I-104, I-105, I-106, I-107, I-108, I-109, I-110, I-111, I-112, I-113, I-114, I-115, I-116, I-117, I-118, I-119, I-120, I-121, I-122, I-123, I-124, I-125, I-126, I-127, I-128, I-129, I-130, I-131, I-132, I-133, I-134, I-135, I-136, I-137, I-138, I-139, I-140, I-141, I-142, I-143, I-144, I-145, I-146, I-147, I-148, I-149, I-150, I-151, I-152, I-153, I-154, I-155, I-156, I-157, I-158, I-159, I-160, I-161, I-162, I-163, I-164, I-165, I-166, I-167, I-168, I-169, I-170, I-171, I-172, I-173, I-174, I-175, I-176, I-177, I-178, I-179, I-180, I-181, I-182, I-183, I-184, I-185, I-186, I-187, I-188, I-189, I-190, I-191, I-192, I-193, I-194, I-195, I-196, I-197, I-198, I-199, I-200, I-201, I-202, I-203, I-204, I-205, I-211, I-212, I-214, I-215, I-216, I-218, I-219, I-220, I-221, I-222, I-223, I-224, I-230, I-231, I-232, I-233, I-235, I-236, I-237, I-238, I-239, I-240, I-241, I-244, I-245, I-246, I-247, I-249, I-250, I-251, I-252, I-253, I-254, I-255, I-256, I-257, I-258, I-259, I-260, I-261, I-262, I-263, I-264, I-265, I-266, I-267, I-268, I-269, I-270, I-271, I-272, I-273, I-274, I-275, I-276, I-277, I-278, I-279, I-280, I-281, I-282, I-283, I-284, I-285, I-286, I-287, I-288, I-289, I-290, I-291, I-292, I-293, I-294, I-295, I-296, I-297, I-298, I-299, I-300, I-301, I-302, I-303, I-304, I-305, I-306, I-307, I-308, I-309, I-310, I-311, I-312, I-313, I-314, I-315, I-316, I-317, I-366, I-367, I-368, I-369, I-370, I-371, I-372, I-373, I-374, I-375, I-376, I-377, I-378, I-379, I-380, I-381, I-382, I-383, and I-384 at 500 ppm showed at least 75% mortality in comparison with untreated controls.

B.2 Cotton Aphid (*Aphis gossypii*, Mixed Life Stages)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds I-1, I-4, I-5, I-6, I-7, I-9, I-10, I-11, I-12, I-13, I-14, I-15, I-16, I-17, I-18, I-20, I-21, I-22, I-23, I-24, I-26, I-27, I-28, I-29, I-30, I-31, I-32, I-33, I-35, I-36, I-38, I-39, I-42, I-43, I-44, I-45, I-46, I-47, I-48, I-51, I-60, I-61, I-62, I-63, I-64, I-66, I-67, I-75, I-76, I-77, I-78, I-79, I-80, I-81, I-83, I-85, I-87, I-88, I-90, I-91, I-92, I-93, I-94, I-95, I-96, I-97, I-98, I-99, I-100, I-101, I-102, I-103, I-104, I-105, I-106, I-107, I-109, I-112, I-114, I-115, I-116, I-117, I-118, I-119, I-120, I-121, I-125, I-129, I-131, I-133, I-134, I-135, I-136, I-137, I-138, I-140, I-141, I-142, I-143, I-144, I-145, I-147, I-148, I-149, I-150, I-151, I-152, I-155, I-157, I-166, I-167, I-168, I-169, I-170, I-173, I-174, I-181, I-182, I-183, I-184, I-185, I-186, I-188, I-189, I-190, I-191, I-192, I-193, I-195, I-196, I-197, I-198, I-199, I-200, I-201, I-202, I-203, I-204, I-205, I-211, I-212, I-232, I-233, I-238, I-265, I-271, I-277, I-290, I-300, I-302, I-307, I-366, I-367, I-368, I-369, I-370, I-371, I-372, I-373, I-374, I-375, I-376, I-377, I-378, I-379, I-380, I-381, I-382, I-383, and I-384 at 10 ppm showed at least 75% mortality in comparison with untreated controls.

B.3 Silverleaf Whitefly (*Bemisia argentifolii*, Adult)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds I-4, I-5, I-6, I-7, I-8, I-9, I-10, I-11, I-12, I-13, I-14, I-18, I-20, I-21, I-22, I-23, I-24, I-27, I-28, I-29, I-30, I-31, I-32, I-33, I-35, I-39, I-43, I-46, I-61, I-63, I-67, I-68, I-76, I-79, I-85, I-87, I-88, I-90, I-91, I-92, I-93, I-94, I-96, I-97, I-98, I-102, I-103, I-104, I-105, I-109, I-113, I-115, I-128, I-129, I-133, I-135, I-137, I-138, I-139, I-142, I-143, I-144, I-145, I-146, I-148, I-149, I-153, I-155, I-157, I-167, I-168, I-169, I-173, I-177, I-181, I-182, I-183, I-184, I-188, I-190, I-198, I-201, I-202, I-204, I-238, I-260, I-266, I-277, I-292, I-366, I-367, I-368, I-369, I-370, I-371, I-372, I-376, I-377, I-379, and I-380 at 10 ppm showed at least 75% mortality in comparison with untreated controls.

B.4 Vetch Aphid (*Megoura viciae*)

The active compounds were formulated in 3:1 (vol:vol) water:DMSO with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiter plates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-38, I-41, I-42, I-43, I-44, I-45, I-46, I-47, I-48, I-49, I-50, I-51, I-52, I-53, I-54, I-55, I-57, I-58, I-59, I-60, I-61, I-62, I-63, I-64, I-65, I-66, I-67, I-68, I-69, I-70, I-71, I-72, I-74, I-75, I-76, I-77, I-78, I-79, I-80, I-81, I-82, I-83, I-84, I-85, I-86, I-87, I-88, I-91, I-92, I-93, I-94, I-95, I-96, I-97, I-98, I-99, I-100, I-101, I-102, I-103, I-104, I-105, I-106, I-107, I-108, I-109, I-112, I-113, I-114, I-115, I-116, I-117, I-118, I-119, I-120, I-121, I-122, I-123, I-124, I-125, I-126, I-127, I-128, I-129, I-130, I-131, I-132, I-133, I-134, I-135, I-136, I-137, I-138, I-140, I-141, I-142, I-143, I-144, I-145, I-146, I-152, I-154, I-155, I-156, I-157, I-158, I-159, I-161, I-162, I-163, I-164, I-165, I-166, I-173, I-174, I-181, I-182, I-183, I-184, I-185, I-194, I-195, I-196, I-197, I-218, I-219, I-220, I-221, I-222, I-223, I-224, I-225, I-226, I-227, I-228, I-229, I-230, I-231, I-232, I-233, I-234, I-242, I-244, I-245, I-246, I-247, I-248, I-256, I-270, I-271, I-272, I-273, I-274, I-275, I-289, I-304, I-305, I-306, I-307, I-308, I-309, I-311, I-312, I-366, I-367, I-368, I-369, I-370, I-371, I-372, I-373, I-374, I-375, I-376, I-377, I-378, I-379, I-380, I-381, I-382, I-383, and I-384 at 2500 ppm showed at least 75% mortality in comparison with untreated controls.

B.5 Green Peach Aphid (*Myzus persicae*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24 hour photoperiod at 25° C. and 20-40% relative humidity. Aphid mortality on the treated plants, relative to mortality on untreated control plants, was determined after 5 days.

In this test, compounds I-1, I-2, I-4, I-5, I-6, I-7, I-8, I-9, I-10, I-11, I-12, I-13, I-14, I-15, I-16, I-17, I-18, I-19, I-20, I-21, I-22, I-23, I-24, I-27, I-28, I-29, I-30, I-31, I-32, I-33, I-34, I-35, I-36, I-37, I-38, I-39, I-42, I-43, I-44, I-45, I-46, I-47, I-48, I-50, I-60, I-61, I-62, I-63, I-64, I-66, I-67, I-69, I-71, I-74, I-75, I-76, I-77, I-78, I-79, I-80, I-81, I-82, I-83, I-84, I-85, I-86, I-87, I-88, I-89, I-90, I-91, I-92, I-93, I-94, I-95, I-96, I-97, I-98, I-99, I-100, I-101, I-102, I-103, I-104, I-105, I-106, I-107, I-108, I-109, I-110, I-111, I-112, I-114, I-115, I-116, I-117, I-118, I-120, I-121, I-124, I-125, I-126, I-127, I-128, I-129, I-130, I-131, I-132, I-133, I-134, I-135, I-136, I-137, I-138, I-140, I-141, I-142, I-143, I-144, I-145, I-146, I-147, I-148, I-149, I-150, I-151, I-152, I-153, I-155, I-157, I-167, I-168, I-169, I-170, I-173, I-174, I-176, I-177, I-181, I-183, I-184, I-185, I-186, I-188, I-189, I-190, I-191, I-192, I-193, I-194, I-195, I-196, I-197, I-198, I-199, I-200, I-201, I-202, I-203, I-204, I-205, I-211, I-212, I-232, I-238, I-251, I-265, I-266, I-271, I-277, I-284, I-288, I-290, I-291, I-292, I-293, I-300, I-302, I-303, I-307, I-366, I-367, I-368, I-369, I-370, I-371, I-372, I-373, I-374, I-375, I-376, I-377, I-378, I-379, I-380, I-381, I-382, I-383, and I-384 at 10 ppm showed at least 75% mortality in comparison with untreated controls.

B.6 Boll Weevil (*Anthonomus grandis*)

The compounds were formulated in 3:1 (vol:vol) water: DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 μl, using a custom built micro atomizer, at two replications. After application, the microtiter plates were incubated at 23±1° C. and 50±5% relative humidity for 5 days. Egg and larval mortality was then visually assessed.

In this test, compounds I-67, I-85, I-92, I-94, I-95, I-96, I-98, I-102, I-104, I-113, I-127, I-132, I-137, I-143, I-182, I-374, I-377, and I-380 at 2500 ppm showed at least 75% mortality in comparison with untreated controls.

B.7 Rice Plant Hopper (*Nilaparvata lugens*)

Rice seedlings were cleaned and washed 24 hours before spraying. The active compounds were formulated in 1:1 (vol:vol) water:aceton and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds I-8, I-9, I-10, I-11, I-25, I-29, I-35, I-62, I-63, I-68, I-113, I-141, I-143, I-199, I-204, I-245, I-312, and I-371 at 500 ppm showed at least 75% mortality in comparison with untreated controls.

B.8 Orchid Thrips (*Dichromothrips corbetti*)

The active compounds were formulated as a 1:1 (vol:vol) water:aceton solution. Surfactant (Alkamuls EL 620) was added at the rate of 0.1% (vol/vol). Vanda orchids petals were cleaned, washed and air dried prior to spraying. Petals were dipped into the test solution for 3 seconds, air dried, placed inside a resealable plastic and inoculated with 20 adults. The treated petals were kept inside the holding room at 28-29° C. and relative humidity of 50-60%. Percent mortality was recorded after 72 hours.

In this test, compounds I-4, I-35, I-39, I-43, I-78, I-83, I-86, I-94, I-95, I-96, I-107, I-109, I-115, I-132, I-133, I-142, I-143, I-146, I-154, I-158, I-168, I-184, I-186, I-187, I-189, I-191, I-193, I-198, I-201, I-202, I-203, I-204, I-205, I-278, I-279, I-280, I-281, I-297, I-298, I-299, I-300, I-305, I-306, I-308, I-310, I-370, and I-373 at 500 ppm showed at least 75% mortality in comparison with untreated controls.

B.9 Rice Green Leafhopper (*Nephotettix virescens*)

Rice seedlings were cleaned and washed 24 hours before spraying. The active compounds were formulated in 1:1 (vol:vol) water:aceton, and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds I-7, I-8, I-10, I-11, I-32, I-33, I-63, I-79, I-113, and I-199 at 500 ppm showed at least 75% mortality in comparison with untreated controls.

B.10 Diamondback Moth (*Plutella xylostella*)

The active compounds were formulated in 1:1 (vol:vol) water:aceton and 0.1% (vol/vol) Alkamuls EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment.

The beneficial activity of the compounds according to the invention over structurally close compounds known from prior art was demonstrated by the following comparative experiments:

The tables show % mortality in comparison to untreated controls.

| Compounds Tests/conc. | #I-32 | #7 of Table 14 in WO10/034737 |
|---|---|---|
| B.1/0.3 ppm | 100% | 0% |
| B.2/3 ppm | 90% | 25% |

| Compounds Tests/conc. | #I-32 | #5 of Table 14 in WO10/034737 |
|---|---|---|
| B.3/1 ppm | 100% | 0% |
| B.9/500 ppm | 75% | 0% |

| Compounds Tests/conc. | #I-98 | #175 in WO10/034737 |
|---|---|---|
| B.1/0.3 ppm | 75% | 0% |
| B.2/0.1 ppm | 95% | 0% |
| B.5/0.1 ppm | 95% | 0% |

| Compounds Tests/conc. | #I-98 | #5 of Table 98 in WO10/034737 |
|---|---|---|
| B.3/3 ppm | 75% | 0% |
| B.10/500 ppm | 25% FD*) | 100% FD*) |

*)FD = feeding damage

| Compounds Tests/conc. | #I-198 | #5 of Table 98 in WO10/034737 |
|---|---|---|
| B.3/1 ppm | 100% | 0% |
| B.8/500 ppm | 75% | 0% |

| Compounds Tests/conc. | #I-201 | #5 of Table 98 in WO10/034737 |
|---|---|---|
| B.3/1 ppm | 100% | 0% |
| B.8/500 ppm | 63% | 0% |

| Compounds Tests/conc. | #I-377 | #173 in WO09/027393 |
|---|---|---|
| B.3/10 ppm | 75% | 25% |
| B.5/10 ppm | 100% | 50% |

| Compounds Tests/conc. | #I-377 | #180 in WO09/0027393 |
|---|---|---|
| B.3/100 ppm | 100% | 0% |

The invention claimed is:

1. A compound of formula I

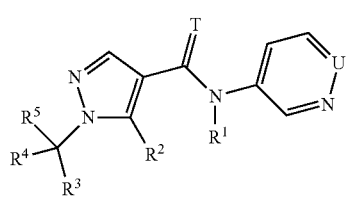

wherein
U is N or CH;
T is O or S;
$R^1$ is H, $C_1$-$C_2$-alkyl, or $C_1$-$C_2$-alkoxy-$C_1$-$C_2$-alkyl;
$R^2$ is $CH_3$, or halomethyl;
$R^3$ is $C_2$-$C_6$-alkyl, $C_1$-$C_6$-haloalkyl, C1-C2-alkoxy-$C_1$-$C_2$-alkyl, $C_2$-$C_6$-alkenyl, $C_2$-$C_6$-alkynyl, $C_3$-$C_6$-cycloalkyl, $C_5$-$C_6$-cycloalkenyl, $C_1$-$C_6$-alkoxy, CN, $NO_2$, or $S(O)_n R^b$, wherein the C-atoms may be unsubstituted, or partially or fully substituted by $R^a$;
$R^a$ is halogen, CN, $NO_2$, $C_1$-$C_2$-alkyl, $C_1$-$C_2$-haloalkyl, $C_1$-$C_4$-alkoxy, $C_1$-$C_2$-haloalkoxy, or $S(O)_n R^b$;
n is 0, 1, or 2;
$R^b$ is hydrogen, $C_1$-$C_2$-alkyl, $C_1$-$C_2$-haloalkyl, $C_3$-$C_6$-cycloalkyl, or $C_1$-$C_4$-alkoxy,
$R^4$ is $C_1$-$C_4$-alkyl, or a group mentioned for $R^3$;
$R^5$ is H, or a group mentioned for $R^4$; or
$R^3$ and $R^4$ together with the carbon to which they are attached form a three- to six-membered carbo- or heterocycle, which may contain 1 or 2 heteroatoms selected from the group consisting of N-$R^c$, O and S, wherein S may be oxidized, which carbo- or heterocycle may be substituted by $R^a$;
$R^c$ is hydrogen, $C_1$-$C_2$-alkyl, $C_1$-$C_2$-haloalkyl, $C_1$-$C_2$-alkylcarbonyl, or $C_1$-$C_2$-alkoxycarbonyl;
or a stereoisomer, a salt, a tautomer or an N-oxide thereof.

2. The compound of claim 1, wherein U is CH.

3. The compound of claim 1, wherein U is N.

4. The compound of claim 1, wherein T is O.

5. The compound of claim 1, wherein $R^1$ is H, $C_1$-$C_2$-alkyl, or $C_1$-$C_2$-alkoxymethyl.

6. The compound of claim 1, wherein $R^2$ is $CH_3$, $CHF_2$, or $CF_3$.

7. The compound of claim 1, wherein $R^3$ is CN, $C_2$-$C_6$-alkyl, $C_1$-$C_2$-haloalkyl, $C_1$-$C_2$-alkoxy-C1-C2-alkyl, or $C_3$-C6-cycloalkyl, wherein the C-atoms may be substituted.

8. The compound of claim 1, wherein $R^4$ is $C_1$-$C_4$-alkyl, $C_1$-C4-haloalkyl, or $C_3$-$C_6$-cycloalkyl, wherein the C-atoms may be substituted.

9. The compound of claim 1, wherein $R^5$ is H or $CH_3$.

10. A composition comprising at least one compound of claim 1 and at least one inert liquid and/or solid carrier.

11. An agricultural composition for combating animal pests comprising at least one compound of claim 1 and at least one inert liquid and/or solid acceptable carrier and, if desired, at least one surfactant.

12. A method for combating or controlling invertebrate pests, which method comprises contacting said pest or its food supply, habitat or breeding grounds with a pesticidally effective amount of at least one compound of claim 1.

13. A method for protecting growing plants from attack or infestation by invertebrate pests, which method comprises contacting a plant, or soil or water in which the plant is growing, with a pesticidally effective amount of at least one compound as defined in claim 1.

14. The method of claim 13, wherein U is CH.

15. The method of claim 13, wherein U is N.

16. The method of claim 13, wherein T is O.

17. The method of claim 13, wherein $R^1$ is H, $C_1$-$C_2$-alkyl, or $C_1$-$C_2$-alkoxymethyl.

18. The method of claim 13, wherein $R^2$ is $CH_3$, $CHF_2$, or $CF_3$.

19. The method of claim 13, wherein $R^3$ is CN, $C_2$-$C_6$alkyl, $C_1$-$C_2$-haloalkyl, $C_1$-$C_2$-alkoxy-$C_1$-$C_2$-alkyl, or $C_3$-$C_6$-cycloalkyl, wherein the C-atoms may be substituted.

20. The method of claim 13, wherein $R^4$ is $C_1$-$C_4$-alkyl, $C_1$-$C_4$-haloalkyl, or $C_3$-$C_6$-cycloalkyl, wherein the C-atoms may be substituted.

* * * * *